United States Patent
Altman et al.

(10) Patent No.: US 9,018,170 B2
(45) Date of Patent: Apr. 28, 2015

(54) REDUCED VOLUME FORMULATION OF GLATIRAMER ACETATE AND METHODS OF ADMINISTRATION

(75) Inventors: Ayelet Altman, Hod-haSharon (IL); Doris Saltkill, Kansas City, MO (US); Tomer El-Gad, Rehovot (IL); Dalton L. Tomlinson, Overland Park, KS (US)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 1172 days.

(21) Appl. No.: 12/948,611

(22) Filed: Nov. 17, 2010

(65) Prior Publication Data

US 2011/0066112 A1   Mar. 17, 2011

Related U.S. Application Data

(63) Continuation of application No. 12/785,125, filed on May 21, 2010, now Pat. No. 7,855,176, which is a continuation of application No. 12/761,367, filed on Apr. 15, 2010, now abandoned.

(60) Provisional application No. 61/271,009, filed on Jul. 15, 2009, provisional application No. 61/271,340, filed on Jul. 20, 2009, provisional application No. 61/337,011, filed on Jan. 29, 2010.

(51) Int. Cl.
*A61K 38/07* (2006.01)
*A61K 9/00* (2006.01)
*A61K 38/16* (2006.01)

(52) U.S. Cl.
CPC ............... *A61K 9/0019* (2013.01); *A61K 38/16* (2013.01)

(58) Field of Classification Search
CPC ....... A61K 38/02; A61K 38/03; A61K 38/04; A61K 38/07; A61K 38/16; A61K 9/0019
See application file for complete search history.

(56) References Cited

U.S. PATENT DOCUMENTS

| | | | |
|---|---|---|---|
| 5,137,516 A | 8/1992 | Rand et al. |
| 5,981,589 A | 11/1999 | Konfino et al. |
| 6,048,898 A | 4/2000 | Konfino et al. |
| 6,054,430 A | 4/2000 | Konfino et al. |
| 6,342,476 B1 | 1/2002 | Konfino et al. |
| 6,362,161 B1 | 3/2002 | Konfino et al. |
| 6,448,225 B2 | 9/2002 | O'Connor et al. |
| 6,620,847 B2 | 9/2003 | Konfino et al. |
| 6,939,539 B2 | 9/2005 | Konfino et al. |
| 7,033,582 B2 | 4/2006 | Yong et al. |
| 7,199,098 B2 | 4/2007 | Konfino et al. |
| 7,442,185 B2 | 10/2008 | Amark et al. |
| 7,560,100 B2 | 7/2009 | Pinchasi et al. |
| 7,585,843 B2 | 9/2009 | Garren et al. |
| 7,655,221 B2 | 2/2010 | Rasmussen et al. |
| 2002/0077278 A1 | 6/2002 | Yong et al. |
| 2004/0039336 A1 | 2/2004 | Amark et al. |
| 2004/0106554 A1 | 6/2004 | Konfino et al. |
| 2006/0154862 A1 | 7/2006 | Ray et al. |
| 2007/0161566 A1 | 7/2007 | Pinchasi |
| 2008/0118553 A1 | 5/2008 | Frenkel et al. |
| 2009/0048181 A1 | 2/2009 | Schipper et al. |
| 2009/0149541 A1 | 6/2009 | Stark et al. |

FOREIGN PATENT DOCUMENTS

| | | |
|---|---|---|
| EP | 1349590 | 5/2006 |
| WO | WO 02/47746 | 6/2002 |
| WO | WO 2006/029036 | 3/2006 |
| WO | WO 2007/081975 | 7/2007 |
| WO | WO 2009/070298 | 6/2009 |
| WO | PCT/US2010/001972 | 7/2010 |

OTHER PUBLICATIONS

U.S. Appl. No. 12/761,367, filed Apr. 15, 2010, Altman, et al.
U.S. Appl. No. 12/806,684, filed Aug. 19, 2010, Klinger.
U.S. Appl. No. 12/861,655, Aug. 23, 2010, Stark and Ladakani.
U.S. Appl. No. 29/370,417, filed Jul. 14, 2010, Tomer El-Gad, et al.
U.S. Appl. No. 29/370,420, filed Jul. 14, 2010, Tomer El-Gad, et al.
U.S. Appl. No. 12/785,125, filed May 21, 2010, Altman, et al.
Apr. 2, 2009 Final Office Action issued in connection with U.S. Appl. No. 11/651,212, filed Jan. 9, 2007 (U.S. Patent Application Publication No. US 2007/0161566).
Jul. 20, 2009 Office Action issued in connection with U.S. Appl. No. 11/651,212, filed Jan. 9, 2007 (U.S. Patent Application Publication No. US 2007/0161566).
Jun. 20, 2008 Office Action issued in connection with U.S. Appl. No. 11/651,212, filed Jan. 9, 2007 (U.S. Patent Application Publication No. US 2007/0161566).
Supplementary European Search Report issued on Jul. 29, 2010 in connection with European Application No. 10160099.7-1219.
Jul. 27, 2010 Office Action issued by the Canadian Intellectual Property Office in connection with Canadian Patent Application No. 2,697,570, filed Apr. 15, 2010.
Dec. 22, 2008 Amendment in Rsp to Jun. 20, 2008 Office Action issued in conn. with U.S. Appl. No. 11/651,212, filed Jan. 9, 2007 (U.S. Patent App.Pub. No. US 2007/0161566).
Jul. 1, 2009 Amendment Under 37 C.F.R. 1.116 in Rsp to Apr. 2, 2009 Final Office Action issued in connection with U.S. Appl. No. 11/651,212, filed Jan. 9, 2007.
Aug. 30, 2010 Response to the Jul. 27, 2010 Office Action issued by the Canadian Patent Office in conn. with Canadian Patent Application No. 2,697,570, filed Apr. 15, 2010.
Anderson, et al. (1992) "Revised estimate of the prevalence of multiple sclerosis in the United States". Ann Neurol. 31:333-36.
Anderson, et al. "Injection pain decreases . . . " The Consortium of Multiple Sclerosis Centers 2010 Annual Meeting, Jun. 2-5, 2010, San Antoinio, Texas (Abstract only).
Arnon and Aharoni (2007) "Neurogenesis and neuroprotection in the CAN . . . ". Mol Neurobiol. 36:245-53.
Bjartmar C, et al. (2002) "Pathological mechanisms and disease progression of multiple sclerosis: therapeutic implications". Drugs of Today. 38:7-29.

(Continued)

*Primary Examiner* — Leslie A. Royds Draper
(74) *Attorney, Agent, or Firm* — John P. White; Gary J. Gershik; Cooper & Dunham LLP

(57) ABSTRACT

A method for reducing frequency of relapses in a human patient afflicted with relapsing-remitting multiple sclerosis (RRMS) comprising administering to the patient 0.5 ml of an aqueous pharmaceutical solution of 20 mg glatiramer acetate and 20 mg mannitol.

6 Claims, 11 Drawing Sheets

(56) References Cited

OTHER PUBLICATIONS

Bornstein, et al. (1987) "A pilot trial of Cop 1 in exacerbating remitting multiple sclerosis". New Eng J Med. 317:408-14.
Bornstein, et al. (1991) "A placebo-controlled, double-blind, randomized, two-center, pilot trial of Cop-1 in chronic progressive multiple sclerosis". Neurology. 41:533-39.
Brazeau GA, et al. (1998) "Current perspectives on pain upon injection of drugs". J Pharmaceutical Sci.(87)6:667-677.
Chantelau e, et al. (1991) "What make insulin injections painful?" BMJ. 303:26-27.
Cohen et al., "Randomized, double-blind, dose-comparison study of glatiramer acetate in relapsing-remitting MS", Neurology, 2007; 68:939-944.
Comi G. "Treatment with glatiramer acetate . . . ". Program and abstracts of the American Academy of Neurology 60th Annual Meeting; Apr. 12-19, 2008; Chicago, Illinois. LBS.003.
Comi, et al. (2001) "European/Canadian multicenter, double-blind, randomized, placebo-controlled . . . ". Ann Neurol. 49:290-7.
Comi, et al. (2008) "Results from a phase III, one-year, randomized, double-blind, parallel-group, dose-comparison . . . ". Mult Scler. 14(suppl 1):S299.
Coyle, PK., "Disease-modifying agents in multiple sclerosis" Ann. Indian Acad. Neurol., Oct.-Dec. 2009; 12(4): 273-282.
Dhib-Jalbut S. (2002) "Mechanisms of action of interferons and glatiramer acetate in multiple sclerosis". Neurology. 58(Suppl 4):S3-S9.
Dhib-Jalbut S. (2003) "Glatiramer acetate (Copaxone) therapy for multiple sclerosis" Pharmacology & Therapeutics. 98:245-55.
Frenken LA, et al. (1994) "Analysis of the efficacy of measures to reduce pain after subcutaneous administration of epoetin alfa". Nephrol Dial Transplant. 9:1295-1298.
Gibson (2004) "Selection of Injection Volume" Pharmaceutical Preformulation and Formulation. p. 332.
Guideline on clinical investigation of medicinal products for the treatment of multiple sclerosis EMEA, London Nov. 16, 2006 CPMP/EWP/561/98 Rev.1.
Johnson, et al. (1998) "Extended use of glatiramer acetate (Copaxone) is well tolerated and . . . " Neurology. 50:701-8.
Jørgensen, et al. (1996) "Pain Assessment of Subcutaneous Injections" Ann Pharmacother. 30(7):729-732.
Kansara, et al. (2009) "Subcutaneous Delivery". Drug Deliv Technol. Jun. 2009; 9(6):38-42.
Medical News Today. Jul. 8,2008. Web: Sep. 9, 2010. www.medicalnewstoday.com/articles/114183.php.
Miller D, et al. (2005) "Clinically isolated syndromes suggestive of multiple sclerosis, part I: natural history . . . ". Lancet Neurol. 4(5):281-288.
Miller D, et al. (2005) "Clinically isolated syndromes suggestive of multiple sclerosis, part II: non-conventional MRI . . . ", Lancet Neurol. 4(6):341-348.
Neuhaus O, et al. (2003) "Immunomodulation in multiple sclerosis: from immunosuppression to neuroprotection". Trends Pharmacol Sci. 24:131-138.
Noseworthy, et al. (2000) "Multiple sclerosis". N Engl J Med. 343:938-52.
Polman, et al, (2005) "Diagnostic Criteria for Multiple Sclerosis: 2005 Revisions to the "McDonald" Criteria". Ann Neurol. 58:840-846.
Pre-Examination Search Report, Feb. 23, 2010 from Envision IP Inc.
Product Monograph, Copaxone, Revised Apr. 2, 2010: 1-35.
Ruggiere, et al. (2007) "Glatiramer acetate in multiple sclerosis: A review". CNS Drug Reviews. 13(2):178-91.
Schrempf W, et al. (2007) "Glatiramer acetate: Mechanisms of action in multiple sclerosis". Autoimmunity Reviews 2007. 6:469-475.
Shire, et al. (2004) "Challenges in the Development of High Protein Concentration Formulations". J Pharm Sci. 93(6):1390-1402.
Teva Press Release, Teva Provides Update on FORTE Trial, Jul. 7, 2008.
The National MS Society (USA) [cited Feb. 5, 2010]. Available from: www.nationalmssociety.org/about-multiple-sclerosis/what-we-know-about-ms/treatments/index.aspx.
Thrower BW, (2007) "Clinically isolated syndromes. Predicting and delaying multiple sclerosis". Neurology. 68 (Suppl 4):S12-S15.
Tselis, et al. (2007) "Glatiramer acetate in the treatment of multiple sclerosis". Neuropsychiatric Dis Treat. 3(2):259-67.
Updated Pre-Examination Search Report, Apr. 9, 2010 from Envision IP Inc.
Van Metre TE, et al. (1996) "Pain and dermal reaction caused by injected glycerin in immunotherapy solutions". J Allergy Clin Immunol. 97:1033-9.
Weber, et al. (2007) "Mechanism of action of glatiramer acetate in treatment of multiple sclerosis". Neurotherapeutics. 4(4):647-53.
Wolinsky, et al. (2007) "Glatiramer acetate in primary progressive multiple sclerosis: Results of a . . . ". Ann Neurol. 61:14-24.
Wolinsky, JS (2006) "The use of glatiramer acetate in the treatment of multiple sclerosis". Adv Neurol. 273-92.
Ziemssen and Schrempf (2007) "Glatiramer acetate: Mechanisms of action in multiple sclerosis". International Rev of Neurobiol. 79:537-70.
Aug. 24, 2010 Office Action issued by the U.S. Patent and Trademark Office in connection with U.S. Appl. No. 12/785,125, filed May 21, 2010.
Nov. 2, 2010 Notice of Allowability issued by the U.S. Patent and Trademark Office in connection with U.S. Appl. No. 12/785,125, filed May 21, 2010.
Sep. 23, 2010 Rsp to Aug. 24, 2010 Office Action Summary of Sep. 15, 2010 Examiner Interview filed in conn. with U.S. Appl. No. 12/785,125, filed May 21, 2010.
International Search Report issued. Jun. 9, 2011 in connection with PCT International Application No. PCT/US2010/001972.
Written Opinion of the International Searching Authority issued Jun. 9, 2011 in connection with PCT International Application Publication No. PCT/US2010/001972.
European Search Report issued Jul. 13, 2010 in connection with European Patent Application Publication No. EP 10160099.7.
Miller, D. et al. (2005) "Clinically isolated syndromes suggestive of multiple sclerosis, part II: non-conventional MRI, recovery process, and management." *Lancet Neurol.* 4(6):341-348.
Neuhaus, O. et al. (2003) "Immunomodulation in multiple sclerosis: from immunesuppression to neuroprotection." *Trends Pharmacol Sci.* 24:131-138.
Noseworthy et al. (2000) "Multiple Sclerosis." *N Eng J Med.* 343:938-952.
Communication pursuant to Article 94(3) EPC issued Feb. 11, 2011 in connection with European Patent Application No. EP 10160099.7.
Jun. 13, 2011 Reply to communication from the Examining Division filed in connection with European Patent Application No. EP 10160099.7.
Decision to grant a European patent pursuant to Article 97(1) EPC issued Feb. 16, 2012 in connection with European Patent Application No. EP 10160099.7.
Notice of opposition to a European patent filed Dec. 11, 2012 in connection with European Patent Application No. EP 10160099.7.
Patient Information Leaflet for Copaxone, cited in Communication of a notice of Opposition, issued Dec. 19, 2012 in connection with European Patent Application No. EP 10160099.7.
Excerpt from "Pharmaceutical Preformulation and Formulation" by M. Gibson, published in 2004, cited in Communication of a notice of Opposition, issued Dec. 19, 2012 in connection with European Patent Application No. EP 10160099.7.
Teva Pharmaceutical Industries Limited Q1 2009 Earnings Call Transcript cited in Communication of a notice of Opposition, issued Dec. 19, 2012 in connection with European Patent Application No. EP 10160099.7.
Front page and excerpt of "Pharmaceutical Preformulation and Formulation" by M. Gibson, published in 2004, cited in Communication of a notice of Opposition, in connection with European Patent Application No. EP 10160099.7.
Reply to the Notice of Opposition against EP2275086B filed by Synthon BV on Aug. 19, 2013 in connection with European Patent Application No. EP 10160099.7.

(56) References Cited

OTHER PUBLICATIONS

Letter regarding opposition procedure filed by patentee on Aug. 19, 2013 in connection with European Patent Application. No. EP 10160099.7.
Amendments to the claim and specification filed by patentee on Aug. 19, 2013 in connection with European Patent Application. No. EP 10160099.7.
Summons to attend oral proceedings pursuant to Rule 115(1) EPC issued Jun. 27, 2014 in connection with European Patent Application No. EP 10160099.7.
Decision to discontinue the opposition proceedings issued Sep. 3, 2014 in connection with European Patent Application No. EP 10160099.7.
Dec. 16, 2013 Non-final rejection Office Action issued by the U.S. Patent and Trademark Office in connection with U.S. Appl. No. 13/384,021.
Mar. 17, 2014 Response to the Dec. 16, 2013 Non-final rejection Office Action issued by the U.S. Patent and Trademark Office in connection with U.S. Appl. No. 13/384,021.
Notice of Allowance issued May 8, 2014 by the U.S. Patent and Trademark Office in connection with U.S. Appl. No. 13/384,021.

REDUCED VOLUME FORMULATION OF GLATIRAMER ACETATE AND METHODS OF ADMINISTRATION

This application is a continuation of U.S. Ser. No. 12/785,125, filed May 21, 2010 now U.S. Pat. No. 7,855,176, which is a continuation of U.S. Ser. No. 12/761,367, filed Apr. 15, 2010 now abandoned, which claims the benefit of U.S. Provisional Application No. 61/271,009, filed Jul. 15, 2009, U.S. Provisional Application No. 61/271,340, filed Jul. 20, 2009 and U.S. Provisional Application No. 61/337,011, filed Jan. 29, 2010, the contents of each of which are hereby incorporated by reference in their entirety.

Throughout this application various publications are referenced by Arabic numeral in parentheses. The full citation of the corresponding reference appears at the end of the specification before the claims. The disclosures of these publications in their entireties are hereby incorporated by reference into this application in order to more fully describe the state of the art to which this invention pertains.

BACKGROUND OF THE INVENTION

Multiple sclerosis (MS) is a chronic, debilitating disease of the central nervous system (CNS) with either relapsing-remitting (RR) or progressive course leading to neurologic deterioration and disability. At time of initial diagnosis, RRMS is the most common form of the disease (1) which is characterized by unpredictable acute episodes of neurological dysfunction (relapses), followed by variable recovery and periods of clinical stability. The vast majority of RRMS patients eventually develop secondary progressive (SP) disease with or without superimposed relapses. Around 15% of patients develop a sustained deterioration of their neurological function from the beginning; this form is called primary progressive (PP) MS. Patients who have experienced a single clinical event (Clinically Isolated Syndrome or "CIS") and who show lesion dissemination on subsequent magnetic resonance imaging (MRI) scans according to McDonald's criteria, are also considered as having relapsing MS (2).

Evidence is accumulating from pathophysiology, pathology, clinical and MRI studies that axonal damage and associated inflammation is characteristic of MS and may occur early in the disease course. It is believed that a confluence of elements must be present for MS to occur: genetic predisposition, immune dysregulation and one or more environmental factors. Although prevalence varies considerably around the world, MS is the most common cause of chronic neurological disability in young adults (3, 4). Anderson et al. estimated that there were about 350,000 physician-diagnosed patients with MS in the United States in 1990 (approx. 140 per 100,000 population) (5). It is estimated that about 2.5 million individuals are affected worldwide (6). In general, there has been a trend toward an increasing prevalence and incidence of MS worldwide, but the reasons for this trend are not fully understood (5).

Current therapeutic approaches consist of i) symptomatic treatment ii) treatment of acute relapses with corticosteroids and iii) treatment aimed to modify the course of the disease. Currently approved therapies target the inflammatory processes of the disease. Most of them are considered to act as immunomodulators but their mechanisms of action have not been completely elucidated. Immunosuppressants or cytotoxic agents are also used in some patients after failure of conventional therapies.

Glatiramer Acetate Injection

Glatiramer acetate (GA) is the active substance in Copaxone®, a marketed product indicated for reduction of the frequency of relapses in patients with RRMS. Glatiramer acetate consists of the acetate salts of synthetic polypeptides containing four naturally occurring amino acids: L-glutamic acid, L-alanine, L-tyrosine and L-lysine. The average molecular weight of glatiramer acetate is between 5,000 and 9,000 Daltons. The marketed medicinal product, Copaxone®, contains 20 mg glatiramer acetate and 40 mg mannitol in 1.0 ml water for injection.

Although extensively researched, the mechanism of action of GA in humans remains uncertain and has been the subject of several recent reviews (7, 8, 9, 10). Based on the preclinical and clinical pharmacology data accumulated in the last four decades of research, it appears that GA's mechanism of action addresses the main pathological mechanisms driving MS, i.e. anti-inflammation, remyelination and neuroprotection (prevention of axonal loss) (11).

The currently available data suggest that after subcutaneous (sc) injection, GA binds HLA class II (DR) on antigen-presenting cells in lymph nodes. As a result, GA can block the activation of myelin-reactive T cells or render these cells anergic. In addition, GA induces GA-specific Th2 cells that cross the blood-brain barrier (BBB) and produce bystander suppression as a result of cross-recognition of myelin antigens. These cells secrete both anti-inflammatory cytokines as well as neurotrophic factors and therefore induce both anti-inflammatory and neuroprotective functions (12).

Clinical experience with GA consists of information obtained from completed and ongoing clinical trials and from post-marketing experience. The clinical program includes three double-blind, placebo-controlled studies in RRMS subjects treated with GA 20 mg/day (13, 14, 15). A significant reduction in the number of relapses, compared with placebo, was seen. In the largest controlled study, the relapse rate was reduced by 32% from 1.98 under placebo to 1.34 under GA 20 mg. GA 20 mg has also demonstrated beneficial effects over placebo on MRI parameters relevant to RRMS. A significant effect in median cumulative number of Gd-enhancing lesions over 9 months of treatment (11 lesions in the 20 mg group compared to 17 lesions under placebo) was demonstrated.

The clinical program with GA also includes one double-blind study in chronic-progressive MS subjects (16), one double-blind placebo-controlled study in primary progressive patients (17), one double-blind placebo-controlled study in CIS patients (20, 21) and numerous open-label and compassionate use studies, mostly in RRMS. The clinical use of GA has been extensively reviewed and published in the current literature (18, 19, 22, 23).

Safety data accumulated for GA in clinical trials shows that the drug product is safe and well tolerated. However, a reaction termed Immediate Post-Injection Reaction (IPIR) consisting of one or more of the following symptoms: vasodilatation, chest pain, dyspnoea, palpitations or tachycardia was reported for 31% of the GA patients vs. 13% on placebo. Additional adverse reactions reported by patients treated with GA 20 mg with at least 2% higher incidence than with placebo were pain, nausea, anxiety, rash, back pain, chills, face edema, local reaction, lymphadenopathy, vomiting, weight increase, tremor, skin disorder, eye disorder, vaginal candidiasis and injection site atrophy.

In all clinical trials, injection-site reactions were seen to be the most frequent adverse reactions and were reported by the majority of patients receiving GA. In controlled studies, the proportion of patients reporting these reactions, at least once, was higher following treatment with GA (70%) than placebo injections (37%). The most commonly reported injection-site reactions, which were more frequently reported in GA vs. placebo-treated patients, were erythema, pain, mass, pruritus, edema, inflammation and hypersensitivity.

Reducing the number and/or severity of the injection-site reactions in order to promote compliance and improving the quality of life for the patient remains a problem with GA treatment. However, for a drug product composed of peptides and whose mechanism of action is not understood, the effects of any modification cannot be readily predicted. Modifications of the formulation may unpredictably affect efficacy. To accommodate an indicated dose requirement in a limited injection volume, a polypeptide drug needs to be delivered at high concentrations. This alone is a significant problem when dealing with peptides of low solubility such as glatiramer acetate which is described as "sparingly soluble" (27). Furthermore, concentrated polypeptide solutions are prone to additional problems. Such formulations suffer from poor shelf-life, unacceptable turbidity, changes in pH, chemical degradation including hydrolysis and aggregation (both reversible and irreversible) and increases in viscosity; all of which potentially reduce shelf-life and bioavailability (25).

Drug administration by subcutaneous injection results in delivery of the drug to the interstitial area underneath the skin. The fluid environment of the interstitial space is essentially that of plasma although the constituent proteins are at a lower concentration. This physiological medium may conflict with the solubility characteristics of the concentrated peptide drug (26). Following injection, the interaction of the delivered drug with the interstitial environment dictates the pattern of absorption of the peptide. Formulation characteristics particularly concentration, injection volume and pH, influence the rate of diffusion and absorption by the patient. Because the interstitium also comprises a fibrous matrix of collagen and glycosaminoglycans, it acts as a barrier to the diffusion and permeability of the drug. As a result, drugs delivered in a concentrated form to the interstitial space may be susceptible to enzymatic degradation at the injection site, precipitation and/or aggregation in the interstitial fluid, and endocytic/phagocytic mechanisms (26). For a peptide drug product such as glatiramer acetate, clinical testing is therefore required to determine whether any modification can effectively reduce the number and severity of injection-site reactions while still substantially maintaining therapeutic efficacy.

SUMMARY OF THE INVENTION

This invention provides a method for reducing frequency of relapses in a human patient afflicted with relapsing-remitting multiple sclerosis (RRMS) comprising administering to the patient by subcutaneous injection 0.5 ml of an aqueous pharmaceutical solution which contains in solution 20 mg glatiramer acetate and 20 mg mannitol.

The invention also provides a method for reducing the frequency of relapse in a human patient who experienced a first clinical episode consistent with multiple sclerosis and who has at least one lesion consistent with multiple sclerosis comprising administering to the patient by subcutaneous injection 0.5 ml of an aqueous pharmaceutical solution which contains in solution 20 mg glatiramer acetate and 20 mg mannitol.

This invention also provides an injection assisting device comprising:
- a first outer shell having a first internal cavity with first and second oppositely arranged openings and
- a second outer shell movably and removably connectable to the first outer shell, the second outer shell being having a second internal cavity with at least a first opening oriented towards the second opening of the first outer shell;
- a button configured to initiate an injection;
- an injection locking member configured to prevent the initiation of an injection in the absence of a predetermined compressive force between the second assembly and the first assembly;
- an injection energy storing member configured to absorb and retain a predetermined amount of injection energy applied to a syringe located within at least one of the first and second cavities during an injection;
- an injection actuator configured, upon the initiation of an injection, to apply the injection energy to the syringe so as to displace a predetermined amount of matter from within the syringe;
- an injection lock indicator configured to indicate to a user whether the injection locking member is in a locked state;
- an injection completion indicator configured to indicate to a user when the predetermined amount of matter has been displaced from within the syringe; and either,
  i) an attention director configured to direct a user's attention to the injection completion indicator,
  ii) an outer grip member formed of a material softer than the second outer shell and disposed an outer surface of the second outer shell; and ridges formed in an outer surface of the outer grip member so as to increase friction between the outer grip member and a human hand, or
  iii) a color of the injection lock indicator is configured to substantially contrast with a color of at least one of the first outer shell and the second outer shell, and the injection lock indicator is configured to be substantially shielded from a view of a user in the presence of the predetermined amount of compression force between the second outer shell and the first outer shell.

This invention provides a syringe pre-filled with 0.5 ml of an aqueous pharmaceutical solution which contains in solution 20 mg glatiramer acetate and 20 mg mannitol.

This invention also provides a unit dose of 0.5 ml of an aqueous pharmaceutical solution which contains in solution 20 mg glatiramer acetate and 20 mg mannitol for use in reducing frequency of relapses in a human patient afflicted with relapsing, remitting multiple sclerosis (RRMS).

This invention additionally provides a unit dose of 0.5 ml of an aqueous pharmaceutical solution which contains in solution 20 mg glatiramer acetate and 20 mg mannitol for use in reducing the frequency of relapse in a human patient who experienced a first clinical episode consistent with multiple sclerosis and who has at least one lesion consistent with multiple sclerosis.

This invention also provides a unit dose of 0.5 ml of an aqueous pharmaceutical solution which contains in solution 20 mg glatiramer acetate and 20 mg mannitol for use in reducing the frequency of relapse in a human patient who experienced a first clinical episode consistent with multiple sclerosis and who has a high risk of developing clinically definite multiple sclerosis (CDMS).

This invention provides a unit dose of 0.5 ml of an aqueous pharmaceutical solution which contains in solution 20 mg glatiramer acetate and 20 mg mannitol for use in reducing the frequency of relapse in a human patient who experienced a first clinical episode consistent with multiple sclerosis and who has at least two clinically silent MRI lesions characteristic of multiple sclerosis.

This invention further provides a use of 0.5 ml of an aqueous pharmaceutical solution which contains in solution 20 mg glatiramer acetate and 20 mg mannitol in the manufacture of a medicament for treating a human patient afflicted with relapsing-remitting multiple sclerosis (RRMS).

This invention yet further provides a use of 0.5 ml of an aqueous pharmaceutical solution which contains in solution 20 mg glatiramer acetate and 20 mg mannitol in the manufacture of a medicament for treating a human patient who experienced a first clinical episode consistent with multiple sclerosis and who has at least one lesion consistent with multiple sclerosis.

This invention also provides a unit dose of 0.5 ml of an aqueous pharmaceutical solution which contains in solution 20 mg glatiramer acetate and 20 mg mannitol for use in treating a human patient who experienced a first clinical episode consistent with multiple sclerosis and who has been determined to be at high risk of developing clinically definite multiple sclerosis (CDMS).

This invention provides a use of 0.5 ml of an aqueous pharmaceutical solution which contains in solution 20 mg glatiramer acetate and 20 mg mannitol in the manufacture of a medicament for treating a human patient who experienced a first clinical episode consistent with multiple sclerosis and who has at least two clinically silent MRI lesions characteristic of multiple sclerosis.

This invention provides a pharmaceutical composition for use in treating a human patient afflicted with relapsing-remitting multiple sclerosis (RRMS) comprising a unit dose of 0.5 ml of an aqueous pharmaceutical solution which contains in solution 20 mg glatiramer acetate and 20 mg mannitol.

This invention also provides a pharmaceutical composition for use in treating a human patient who experienced a first clinical episode consistent with multiple sclerosis and who has at least one lesion consistent with multiple sclerosis comprising a unit dose of 0.5 ml of an aqueous pharmaceutical solution which contains in solution 20 mg glatiramer acetate and 20 mg mannitol.

This invention provides a method of treating a patient suffering from a relapsing form of multiple sclerosis which comprises periodically administering to the patient by subcutaneous injection a 20 mg dose of a pharmaceutical composition, wherein the subcutaneous injection is delivered by automatic injection and wherein the pharmaceutical composition comprises 20 mg of glatiramer acetate in 0.5 ml of solution so as to thereby treat the patient.

This invention provides a unit dose of 0.5 ml of an aqueous pharmaceutical solution which contains in solution 20 mg glatiramer acetate and 20 mg mannitol for use in decreasing the frequency of clinical exacerbations or reducing the number and volume of active MRI brain lesions in a human patient afflicted with relapsing-remitting multiple sclerosis (RRMS).

This invention also provides a unit dose of 0.5 ml of an aqueous pharmaceutical solution which contains in solution 20 mg glatiramer acetate and 20 mg mannitol for use in delaying the onset of Clinically Definite Multiple Sclerosis or decreasing the number and volume of active MRI brain lesions in a human patient who experienced a single demyelinating event and who is considered to be at risk of developing Clinically Definite Multiple Sclerosis.

This invention provides a use of 0.5 ml of an aqueous pharmaceutical solution which contains in solution 20 mg glatiramer acetate and 20 mg mannitol for decreasing the frequency of clinical exacerbations or reducing the number and volume of active MRI brain lesions in a human patient afflicted with relapsing-remitting multiple sclerosis (RRMS).

This invention also provides a use of 0.5 ml of an aqueous pharmaceutical solution which contains in solution 20 mg glatiramer acetate and 20 mg mannitol for delaying the onset of clinically definite multiple sclerosis or decreasing the number and volume of active MRI brain lesions in a human patient who experienced a single demyelinating event and who is considered to be at risk of developing clinically definite multiple sclerosis.

This invention provides a pharmaceutical composition for use in treating a human patient afflicted with relapsing-remitting multiple sclerosis (RRMS) comprising a unit dose of 0.5 ml of an aqueous pharmaceutical solution which contains in solution 20 mg glatiramer acetate and 20 mg mannitol.

This invention provides a pharmaceutical composition for use in treating a human patient who experienced a single demyelinating event and who is considered to be at risk of developing clinically definite multiple sclerosis comprising a unit dose of 0.5 ml of an aqueous pharmaceutical solution which contains in solution 20 mg glatiramer acetate and 20 mg mannitol.

DETAILED DESCRIPTION OF THE INVENTION

Figure 1:
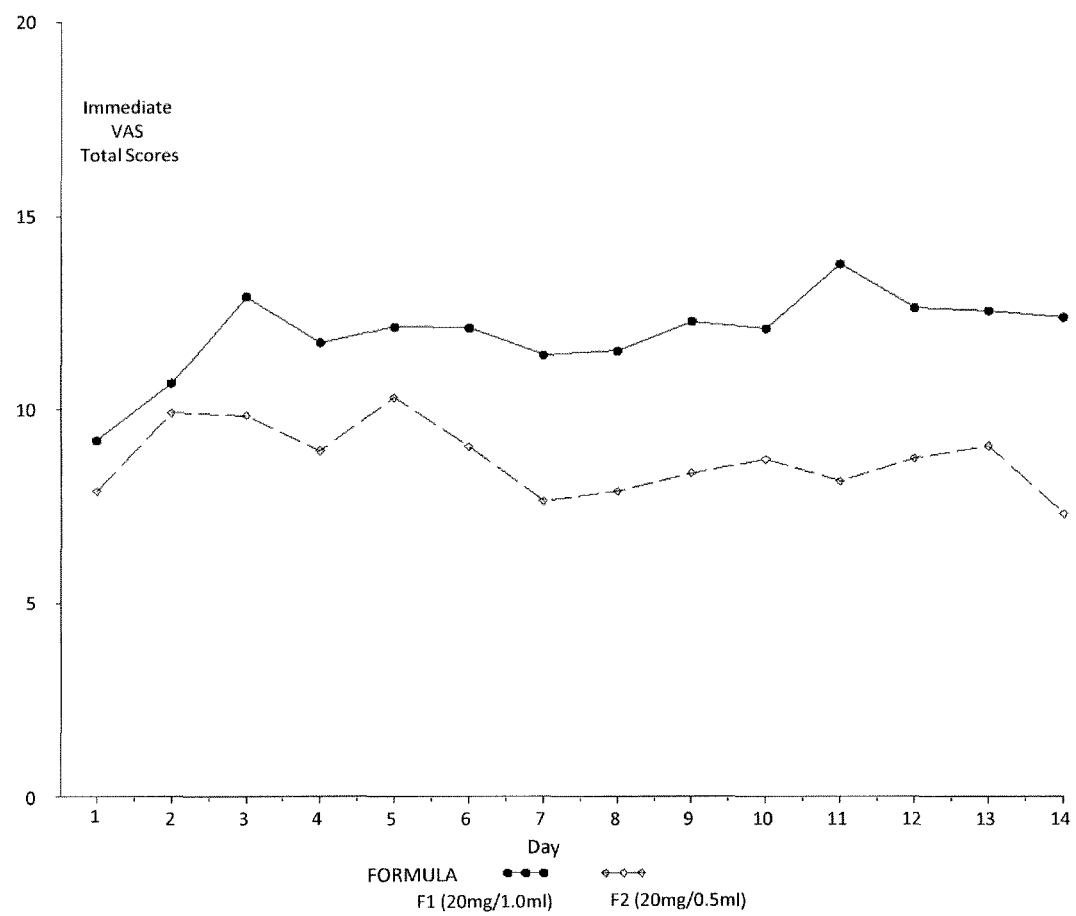
FIG. 1.
Plot of daily total immediate VAS total scores for the ITT population
FIG. 2.
Plot of daily total immediate VAS total scores for the PP population.

This invention provides a method for reducing frequency of relapses in a human patient afflicted with relapsing-remitting multiple sclerosis (RAMS) comprising administering to the patient by subcutaneous injection 0.5 ml of an aqueous pharmaceutical solution which contains in solution 20 mg glatiramer acetate and 20 mg mannitol.

The invention also provides a method for reducing the frequency of relapse in a human patient who experienced a first clinical episode consistent with multiple sclerosis and who has at least one lesion consistent with multiple sclerosis comprising administering to the patient by subcutaneous injection 0.5 ml of an aqueous pharmaceutical solution which contains in solution 20 mg glatiramer acetate and 20 mg mannitol.

According to any embodiment of the methods disclosed herein, the pH of the aqueous pharmaceutical solution is 5.5 to 7.0.

According to any embodiment of the methods disclosed herein, the 20 mg of glatiramer acetate does not form polypeptide aggregates in the 0.5 ml of aqueous pharmaceutical solution.

According to any embodiment of the methods disclosed herein, the 20 mg of glatiramer acetate does not precipitate in the subcutaneous environment after injection.

According to any embodiment of the methods disclosed herein, the 20 mg of glatiramer acetate is absorbed by the patient after the subcutaneous injection.

According to any embodiment of the methods disclosed herein, the 20 mg of glatiramer acetate in 0.5 ml of solution is absorbed by the patient at least as readily as 20 mg of glatiramer acetate in 1 ml of solution.

According to any embodiment of the methods disclosed herein, the 20 mg of glatiramer acetate in 0.5 ml of solution is co-injected with a vasodilator.

According to any embodiment of the methods disclosed herein, the 20 mg of glatiramer acetate in 0.5 ml of solution is co-injected with a vasoconstrictor.

According to any embodiment of the methods disclosed herein, 20 mg of glatiramer acetate in 0.5 ml of solution is co-injected with an extracellular matrix-modifying enzyme.

According to any embodiment of the methods disclosed herein, the subcutaneous injection is administered to the upper back portion of the arm, to the stomach area outside of a 2 inch area around the navel, to the upper outer-rear quadrant of the buttocks, or to the front and outer area of the thigh 2 inches above the knee and 2 inches below the groin.

According to any embodiment of the methods disclosed herein, the pain associated with the subcutaneous injection is reduced relative to pain associated with subcutaneous injection of 1.0 ml of an aqueous pharmaceutical solution of 20 mg glatiramer acetate and 40 mg mannitol.

In an embodiment of the methods disclosed, the pain is the patient-reported total injection pain rating on a visual analogue scale (VAS) occurring immediately after injection.

In a further embodiment of the methods disclosed, the patient-reported total injection pain rating is reduced by about 27%.

In another embodiment of the methods disclosed, the pain is the patient-reported total injection pain rating on a visual analogue scale (VAS) experienced five minutes following subcutaneous injection.

In a further embodiment of the methods disclosed, the patient-reported total injection pain rating experienced five minutes following subcutaneous injection is reduced by about 31%.

In another embodiment of the methods disclosed, the pain is the immediate pain presence following the subcutaneous injection.

In yet another embodiment of the methods disclosed, the immediate pain presence is reduced by about 19%.

In an embodiment of the methods disclosed, the pain is pain presence five minutes following the subcutaneous injection.

In an additional embodiment of the methods disclosed, the pain presence five minutes following the subcutaneous injection is reduced by about 19%.

In yet another embodiment of the methods disclosed, the total number or total severity of Local Injection Site Reactions (LISRs) is reduced relative to the total number or total severity of LISRs associated with subcutaneous injection of 1.0 ml of an aqueous pharmaceutical solution of 20 mg glatiramer acetate and 40 mg mannitol.

In a further embodiment of the methods disclosed, the total number or total severity of Local Injection Site Reactions (LISRs) five minutes after subcutaneous injection is reduced.

In yet a further embodiment of the methods disclosed, the total number of Local Injection Site Reactions (LISRs) five minutes after the subcutaneous injection is reduced by about 24%.

In an additional embodiment of the methods disclosed, the total severity of Local Injection Site Reactions (LISRs) five minutes after the subcutaneous injection is reduced by about 29%.

In an embodiment of the methods disclosed, the total number or total severity of Local Injection Site Reactions (LISRs) 24 hours after subcutaneous injection of glatiramer is reduced.

In another embodiment of the methods disclosed, the total number of Local Injection Site Reactions (LISRs) 24 hours after the subcutaneous injection is reduced by about 23%.

In yet another embodiment of the methods disclosed, the total severity of Local Injection Site Reactions (LISRs) 24 hours after the subcutaneous injection is reduced by about 25%.

According to any embodiment of the methods disclosed herein, the daily five-minute Local Injection Site Reaction (LISR) score is reduced relative to the daily 5-minute LISR score associated with subcutaneous injection of 1.0 ml of an aqueous pharmaceutical solution of 20 mg glatiramer acetate and 40 mg mannitol.

According to any embodiment of the methods disclosed herein, the daily 24-hour Local Injection Site Reaction (LISR) score is reduced relative to the daily 24-hour LISR score associated with subcutaneous injection of 1.0 ml of an aqueous pharmaceutical solution of 20 mg glatiramer acetate and 40 mg mannitol.

In an additional embodiment of the methods disclosed, the Local Injection Site Reactions (LISRs) comprise redness, itching and formation of a lump.

In yet another embodiment of the methods disclosed, the percent of patients who report no Local Injection Site Reactions (LISRs) 5-minutes after injection is increased relative to the percent of patients who report no LISRs 5-minutes after subcutaneous injection of 1.0 ml of an aqueous pharmaceutical solution of 20 mg glatiramer acetate and 40 mg mannitol.

In a further embodiment of the methods disclosed, the percent of patients who report no Local Injection Site Reactions (LISRs) is increased by 3 fold.

In an embodiment of the methods disclosed, the percent of patients who report no Local Injection Site Reactions (LISRs) 24-hours after injection is increased relative to the percent of patients who report no LISRs 24-hours after subcutaneous injection of 1.0 ml of an aqueous pharmaceutical solution of 20 mg glatiramer acetate and 40 mg mannitol.

In an additional embodiment of the methods disclosed, the percent of patients who report no Local Injection Site Reactions (LISRs) is increased by about 50%.

According to any embodiment of the methods disclosed herein, the 0.5 ml aqueous pharmaceutical solution is in a pre-filled syringe.

In yet another embodiment of the methods disclosed, the administration is by an automated subcutaneous injection device containing the prefilled syringe and a means for initiating the subcutaneous injection, completing the subcutaneous injection and indicating to the user that the subcutaneous injection of the 0.5 ml aqueous pharmaceutical solution is complete.

In a further embodiment of the methods disclosed, the 0.5 ml of an aqueous pharmaceutical solution which contains in solution 20 mg glatiramer acetate and 20 mg mannitol is at least as effective as 1.0 ml of an aqueous pharmaceutical solution of 20 mg glatiramer acetate and 40 mg mannitol in reducing the frequency of relapses in a human patient afflicted with relapsing-remitting multiple sclerosis (RAMS).

This invention also provides an injection assisting device comprising:
- a first outer shell having a first internal cavity with first and second oppositely arranged openings and
- a second outer shell movably and removably connectable to the first outer shell, the second outer shell being having a second internal cavity with at least a first opening oriented towards the second opening of the first outer shell;
- a button configured to initiate an injection;
- an injection locking member configured to prevent the initiation of an injection in the absence of a predetermined compressive force between the second assembly and the first assembly;
- an injection energy storing member configured to absorb and retain a predetermined amount of injection energy applied to a syringe located within at least one of the first and second cavities during an injection;
- an injection actuator configured, upon the initiation of an injection, to apply the injection energy to the syringe so as to displace a predetermined amount of matter from within the syringe;
- an injection lock indicator configured to indicate to a user whether the injection locking member is in a locked state;
- an injection completion indicator configured to indicate to a user when the predetermined amount of matter has been displaced from within the syringe; and either,
    i) an attention director configured to direct a user's attention to the injection completion indicator,
    ii) an outer grip member formed of a material softer than the second outer shell and disposed an outer surface of the second outer shell; and ridges formed in an outer surface of the outer grip member so as to increase friction between the outer grip member and a human hand, or
    iii) a color of the injection lock indicator is configured to substantially contrast with a color of at least one of the first outer shell and the second outer shell, and the injection lock indicator is configured to be substantially shielded from a view of a user in the presence of the predetermined amount of compression force between the second outer shell and the first outer shell.

In an additional embodiment of the device disclosed, the injection assisting device further comprising:
- an injection force storage indicator configured to indicate to a user whether at least the predetermined amount of injection energy is stored in the injection energy storing member.

In another embodiment of the device disclosed, the injection assisting device further comprising:
- an outer grip member formed of a material softer than the second outer shell and disposed an outer surface of the second outer shell; and
- ridges formed in an outer surface of the outer grip member so as to increase friction between the outer grip member and a human hand.

In yet another embodiment of the device disclosed, a color of the injection lock indicator is configured to substantially contrast with a color of at least one of the first outer shell and the second outer shell, and
- the injection lock indicator is configured to be substantially shielded from a view of a user in the presence of the predetermined amount of compression force between the second outer shell and the first outer shell.

In a further embodiment of the device disclosed, a color of the attention director is configured to substantially contrast with a color of proximally located components, and
- a shape of the attention director is configured to direct a user's attention to the injection completion indicator.

This invention provides a unit dose of 0.5 ml of an aqueous pharmaceutical solution which contains in solution 20 mg glatiramer acetate and 20 mg mannitol. According to any embodiment of the methods disclosed herein, the 20 mg of glatiramer acetate does not form polypeptide aggregates in the 0.5 ml of aqueous pharmaceutical solution. In an additional embodiment the aqueous pharmaceutical solution has a pH of 5.5-7.0. In another embodiment, the aqueous pharmaceutical solution is in a prefilled syringe.

This invention also provides a unit dose of 0.5 ml of an aqueous pharmaceutical solution which contains in solution 20 mg glatiramer acetate and 20 mg mannitol for use in reducing frequency of relapses in a human patient afflicted with relapsing, remitting multiple sclerosis (RRMS).

This invention additionally provides a unit dose of 0.5 ml of an aqueous pharmaceutical solution which contains in solution 20 mg glatiramer acetate and 20 mg mannitol for use in reducing the frequency of relapse in a human patient who experienced a first clinical episode consistent with multiple sclerosis and who has at least one lesion consistent with multiple sclerosis.

This invention also provides a unit dose of 0.5 ml of an aqueous pharmaceutical solution which contains in solution 20 mg glatiramer acetate and 20 mg mannitol for use in reducing the frequency of relapse in a human patient who experienced a first clinical episode consistent with multiple sclerosis and who has been determined to be at high risk of developing clinically definite multiple sclerosis (CDMS).

This invention provides a unit dose of 0.5 ml of an aqueous pharmaceutical solution which contains in solution 20 mg glatiramer acetate and 20 mg mannitol for use in reducing the frequency of relapse in a human patient who experienced a first clinical episode consistent with multiple sclerosis and who has at least two clinically silent MRI lesions characteristic of multiple sclerosis.

This invention further provides a use of 0.5 ml of an aqueous pharmaceutical solution which contains in solution 20 mg glatiramer acetate and 20 mg mannitol in the manufacture of a medicament for treating a human patient afflicted with relapsing-remitting multiple sclerosis (RRMS).

This invention yet further provides a use of 0.5 ml of an aqueous pharmaceutical solution which contains in solution 20 mg glatiramer acetate and 20 mg mannitol in the manufacture of a medicament for treating a human patient who experienced a first clinical episode consistent with multiple sclerosis and who has at least one lesion consistent with multiple sclerosis.

This invention also provides a unit dose of 0.5 ml of an aqueous pharmaceutical solution which contains in solution 20 mg glatiramer acetate and 20 mg mannitol for use in treating a human patient who experienced a first clinical episode consistent with multiple sclerosis and who has been determined to be at high risk of developing clinically definite multiple sclerosis (CDMS).

This invention provides a use of 0.5 ml of an aqueous pharmaceutical solution which contains in solution 20 mg glatiramer acetate and 20 mg mannitol in the manufacture of a medicament for treating a human patient who experienced a first clinical episode consistent with multiple sclerosis and who has at least two clinically silent MRI lesions characteristic of multiple sclerosis.

This invention provides a pharmaceutical composition for use in treating a human patient afflicted with relapsing-remitting multiple sclerosis (RRMS) comprising a unit dose of 0.5 ml of an aqueous pharmaceutical solution which contains in solution 20 mg glatiramer acetate and 20 mg mannitol.

This invention also provides a pharmaceutical composition for use in treating a human patient who experienced a first clinical episode consistent with multiple sclerosis and who has at least one lesion consistent with multiple sclerosis comprising a unit dose of 0.5 ml of an aqueous pharmaceutical solution which contains in solution 20 mg glatiramer acetate and 20 mg mannitol.

This invention provides a method of treating a patient suffering from a relapsing form of multiple sclerosis which comprises periodically administering to the patient by subcutaneous injection a 20 mg dose of a pharmaceutical composition, wherein the subcutaneous injection is delivered by automatic injection and wherein the pharmaceutical composition comprises 20 mg of glatiramer acetate in 0.5 ml of solution so as to thereby treat the patient.

In an embodiment of the methods disclosed, the injection of 20 mg glatiramer acetate in 0.5 ml of solution is as effective as injection of 20 mg of glatiramer acetate in 1 ml of solution.

In another embodiment of the methods disclosed, the 20 mg of glatiramer acetate in 0.5 ml of solution has a pH equivalent to that of 20 mg of glatiramer acetate in 1 ml of solution.

In yet another embodiment of the methods disclosed, the 20 mg of glatiramer acetate is completely soluble in 0.5 ml of solution.

This invention provides a unit dose of 0.5 ml of an aqueous pharmaceutical solution which contains in solution 20 mg glatiramer acetate and 20 mg mannitol for use in decreasing the frequency of clinical exacerbations or reducing the number and volume of active MRI brain lesions in a human patient afflicted with relapsing-remitting multiple sclerosis (RRMS).

This invention also provides a unit dose of 0.5 ml of an aqueous pharmaceutical solution which contains in solution 20 mg glatiramer acetate and 20 mg mannitol for use in delaying the onset of clinically definite multiple sclerosis or decreasing the number and volume of active MRI brain lesions in a human patient who experienced a single demyelinating event and who is considered to be at risk of developing clinically definite multiple sclerosis.

This invention provides a use of 0.5 ml of an aqueous pharmaceutical solution which contains in solution 20 mg glatiramer acetate and 20 mg mannitol for decreasing the frequency of clinical exacerbations or reducing the number and volume of active MRI brain lesions in a human patient afflicted with relapsing-remitting multiple sclerosis (RRMS).

This invention also provides a use of 0.5 ml of an aqueous pharmaceutical solution which contains in solution 20 mg glatiramer acetate and 20 mg mannitol for delaying the onset of clinically definite multiple sclerosis or decreasing the number and volume of active MRI brain lesions in a human patient who experienced a single demyelinating event and who is considered to be at risk of developing clinically definite multiple sclerosis.

This invention provides a pharmaceutical composition for use in treating a human patient afflicted with relapsing-remitting multiple sclerosis (RRMS) comprising a unit dose of 0.5 ml of an aqueous pharmaceutical solution which contains in solution 20 mg glatiramer acetate and 20 mg mannitol.

This invention provides a pharmaceutical composition for use in treating a human patient who experienced a single demyelinating event and who is considered to be at risk of developing clinically definite multiple sclerosis comprising a unit dose of 0.5 ml of an aqueous pharmaceutical solution which contains in solution 20 mg glatiramer acetate and 20 mg mannitol.

An embodiment of the use, unit dose or pharmaceutical composition disclosed herein, adapted for subcutaneous injection, wherein the 20 mg of glatiramer acetate is absorbed by the patient after the subcutaneous injection.

Another embodiment of the use, unit dose or pharmaceutical composition disclosed herein, adapted for subcutaneous injection to the upper back portion of the arm, to the stomach area outside of a 2 inch area around the navel, to the upper outer-rear quadrant of the buttocks, or to the front and outer area of the thigh 2 inches above the knee and 2 inches below the groin.

Definitions

As used herein, a patient at risk of developing MS (i.e. clinically definite MS) is a patient presenting any of the known risk factors for MS. The known risk factors for MS include anyone of a clinically isolated syndrome (CIS), a single attack suggestive of MS without a lesion, the presence of a lesion (in any of the CNS, PNS, or myelin sheath) without a clinical attack, environmental factors (geographical location, climate, diet, toxins, sunlight) (31, 32, 33), genetics (variation of genes encoding HLA-DRB1, IL7R-alpha and IL2R-alpha) (34, 35), and immunological components (viral infection such as by Epstein-Barr virus, high avidity CD4+ T cells, CD8+ T cells, anti-NF-L, antiCSF114(Glc)) (36, 37, 38).

As used herein, clinically isolated syndrome (CIS) refers to 1) a single clinical attack (used interchangeably herein with "first clinical event" and "first demyelinating event") suggestive of MS, which, for example, presents as an episode of optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning, and 2) at least one lesion suggestive of MS. In a specific example, CIS diagnosis would be based on a single clinical attack and at least 2 lesions suggestive of MS measuring 6 mm or more in diameter.

Visual Analogue Scale (VAS):

As used herein, the VAS is a measurement instrument that tries to measure a characteristic that is believed to range across a continuum of values and cannot easily be directly measured. The amount of pain that a patient feels ranges across a continuum from "no pain" to "worst possible pain". From the patient's perspective this spectrum appears continuous; their pain does not take discrete jumps, as a categorization of none, mild, moderate and severe would suggest. The VAS is a horizontal line, 100 mm in length, anchored by the above word descriptors at each end. The patient marks on the line the point that they feel represents their perception of their current state. The VAS score is determined by measuring in millimeters from the left hand end of the line to the point that the patient marks.

As used herein, "patient-reported total injection pain" refers to pain occurring after the injection as recorded on a 100 mm VAS, where 0 mm represents "no pain" and 100 mm represents "worst possible pain."

As used herein, "immediate pain presence" refers to whether pain is present immediately after injection, wherein pain scores recorded on a 100 mm VAS are dichotomized as either No Pain=0 (if the VAS score is 0-4 mm), or Pain=1 (if the VAS score is 5-100 mm).

LISRs:
Local injection site reactions manifesting as redness, itching, swelling, and/or a lump at the site of injection.

As used herein "subcutaneous injection" refers to delivery of a bolus to the interstitial area underlying the dermis of the skin.

Relapses:
Relapses (also referred to as "exacerbations" or "clinical exacerbations") are characterized by the occurrence of neurological dysfunction symptoms, appearing after a 30-day period of stability or improvement and lasting for more than 24 hours (no infection, no fever). The number of relapses are analyzed using a logistic regression model controlling for treatment and age.

"Relapse Rate" is the number of confirmed relapses per unit time. "Annualized relapse rate" is the mean value of the number of confirmed relapses per each patient multiplied by 365 and divided by the number of days on study drug per each patient.

Forms of Multiple Sclerosis:
There are five distinct disease stages and/or types of MS:
1) benign multiple sclerosis;
2) relapsing-remitting multiple sclerosis (RRMS);
3) secondary progressive multiple sclerosis (SPMS);
4) progressive relapsing multiple sclerosis (PRMS); and
5) primary progressive multiple sclerosis (PPMS)

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.

Patients suffering from RRMS experience sporadic exacerbations or relapses, as well as periods of remission. Lesions and evidence of axonal loss may or may not be visible on MRI for patients with RRMS.

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS (28).

A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesions go on to develop MS, while approximately 20 percent have a self-limited process (29, 30).

Multiple sclerosis may present with optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

Relapsing Form of Multiple Sclerosis:
The term relapsing MS includes:
1) patients with RRMS;
2) patients with SPMS and superimposed relapses; and
3) patients with CIS who show lesion dissemination on subsequent MRI scans according to McDonald's criteria.

As used herein, relapsing forms of multiple sclerosis include: Relapsing-remitting multiple sclerosis (RRMS), characterized by unpredictable acute episodes of neurological dysfunction (relapses), followed by variable recovery and periods of clinical stability;

Secondary Progressive MS (SPMS), wherein patients having RRMS develop sustained deterioration with or without relapses superimposed; and Primary progressive-relapsing multiple sclerosis (PPRMS) or progressive-relapsing multiple sclerosis (PRMS), an uncommon form wherein patients developing a progressive deterioration from the beginning can also develop relapses later on.

As used herein, "about" in the context of a numerical value or range means±10% of the numerical value or range recited or claimed.

As used herein, "active MRI brain lesions" refers to active brain lesions identified on Magnetic Resonance Imaging (MRI) scans.

The unit dose disclosed herein can be administered daily, every other day, weekly, twice weekly, three times weekly, four times weekly, five times weekly or six times weekly.

EXAMPLE 1

Evaluating Subject-Reported Injection Pain Associated with Injections of a 20 mg/0.5 ml Formulation of GA A multicenter, randomized, two arm, single crossover study was undertaken to compare the subject-reported pain of GA 20 mg/1.0 ml (F1) versus GA 20 mg/0.5 ml (F2) administered subcutaneously in subjects with RRMS. Safety and tolerability of the F2 formulation were also assessed. Subjects received both doses once daily in a cross over fashion, for a total treatment duration of five (5) weeks. Subject-reported injection pain was recorded in a daily diary. The primary endpoint was the difference in daily subject-reported injection pain occurring immediately after the injection, for the two GA formulations (F1 versus F2), as recorded on a 100 mm VAS. Secondary objectives included:

To compare subject-reported injection pain associated with injections of F1 versus F2 5 minutes following injection.

To compare the subject-reported presence or absence of Local Injection Site Reactions (LISRs) and degree of severity with injections of F1 versus F2 within the 5-minute period following injection.

To compare the subject-reported presence or absence of LISRs and degree of severity with injections of F1 versus F2 occurring within the 24-hour period following injection.

Methods

At screening, all subjects (and/or caregiver, if applicable) were provided information on manual injection, site rotation and injection site reaction management. The study consisted of a seven day run-in period prior to a fourteen day treatment period of either F1 or F2 (Period 1) and crossover to an additional fourteen day treatment period with the alternate treatment (Period 2). There were four planned study visits: Visit 1 (screening), Visit 2, Visit 3, and Visit 4 (end of study).

148 subjects were randomized to either Sequence F1/F2 (n=76) or Sequence F2/F1 (n=72). A total of 147 (99.3%) subjects received study medication and were analyzed as the safety population; a total of 144 (97.3%) subjects qualified for the intent-to-treat (ITT) population and 139 (93.9%) subjects for the per protocol (PP) population. Of the 148 randomized subjects, 142 (95.9%) subjects completed the study. The reasons for discontinuation were withdrawal of consent (5 [3.4%] subjects) and protocol violation (1 [0.7%] subject). Five subjects were excluded from the PP population due to protocol deviations of treatment non-compliance, intake of prohibited medication, and not meeting inclusion criteria.

Rationale for Study Design, Dose and Population

The purpose of the study was to provide comparative data between a new 20 mg/0.5 ml formulation (F2) of GA and the known profile of the currently marketed 20 mg/1.0 ml formulation (F1). This study was performed in subjects with RRMS who have been on the currently marketed formulation of GA (F1) for a minimum of 90 days.

This study was designed to compare subject-reported pain associated with injection of the 20 mg/1.0 ml formulation (F1) of GA versus a new 20 mg/0.5 ml formulation of GA (F2) immediately after and at five minutes following injections. Additionally, the study compared the presence of local injection site reactions (LISRs), severity of LISRs present and adverse events. Evidence was gathered to assess the safety of the 20 mg/0.5 ml formulation.

The crossover study design was chosen to allow each eligible subject to use the 20 mg/1.0 ml and the 20 mg/0.5 ml formulation for comparable lengths of time. The two week duration of each cross over period was of sufficient length to determine if differences between the two formulations, as defined by the study outcomes, exist. Each subject served as his/her own control, thereby, reducing subject variability and increasing statistical power in comparison of the two formulations. Blinding in this study was not possible due to the subjects' ability to detect differences in the volume of each formulation. The lack of blinding in this study was a known limitation.

Study Population 148 subjects who met the inclusion/exclusion criteria were enrolled.

Inclusion Criteria

Subjects must have met all of the following inclusion criteria in order to be eligible for the study:

Subjects >18 years of age with a diagnosis of RRMS.

Currently injecting GA 20 mg/1.0 ml per day subcutaneously (SC) for a minimum of 90 days utilizing the Autoject®2 for glass syringe or by a manual injection technique.

Willing to switch from Autoject®2 for glass syringe to manual injection technique or continuing with a manual injection technique during the course of the study.

Willing and able to be trained on a seven site injection rotation. Subject must be willing to comply with a minimum five injection site rotation plan during the study.

Willing and able to complete all procedures and evaluations related to the study.

Willing to continue to follow usual injection site preparation and routine adjunctive LISR management techniques.

Willing and able to provide written informed consent.

Exclusion Criteria

Subjects meeting any of the following exclusion criteria were not eligible for study participation:

Currently using or treatment with another immunomodulating therapy (IMT) in conjunction with GA in the 30 days prior to screening for this study.

Currently using intermittent or pulse courses of corticosteroids by any route of administration in the days prior to screening for this study (Corticosteroids are prohibited for the duration of the study).

Currently using an investigational drug or using treatment with any other investigational agent in the 30 days prior to screening for this study.

Presence or history of skin necrosis.

Known extensive dermatological condition that could be a confounding factor.

Pregnant or planning pregnancy or breastfeeding.

Any physical condition that impairs ability to be injected at the minimum of five (5) sites rotation.

Not able or willing to complete a daily diary.

Use of any other parenteral medications [e.g., intramuscular (IM), SC, intravenous (IV), etc.] either currently or in the past 30 days prior to screening for this study.

Any other medical or psychiatric conditions that would make the subject unsuitable for this research, as determined by the Investigator.

Previous participation in this study.

Early Treatment Discontinuation

An end-of-study visit was completed for all subjects who prematurely discontinued from the study. This included subjects who were screened and received at least one dose of study drug, including the run-in period.

Criteria for Early Treatment Discontinuation

The following events/criteria were considered sufficient reason for a subject to discontinue from study medication:

Subject withdrew consent

Sponsor requested subject to be withdrawn

Request of primary care physician or investigator

Protocol violation/non-compliance

Loss to follow-up/failure to return

Adverse event (AE)

Pregnancy

Death

Treatment failure

Other

If an early discontinued subject refused to continue in the study according to the scheduled visits and an AE was present at the last visit, the subject was followed until the medical condition returned to baseline or was considered stable or chronic. If a subject was withdrawn due to AEs, the appropriate AE sections of the case report form (CRF) were completed and the clinical management or monitor was immediately informed of any withdrawal.

In case of manifestation of a severe degree of intolerance to the study drug and/or ongoing exacerbation, the subject was allowed to prematurely discontinue at the discretion of the investigator and the subject was followed until stabilization of the above-mentioned conditions. Subjects who withdrew from the study early were replaced at the discretion of the sponsor.

Disposition of Subjects

Table 1 summarizes the subject disposition in the study. All of 148 subjects screened were randomized to either Sequence F1/F2 (n=76) or Sequence F2/F1 (n=72). Overall, 142 (95.9%) subjects completed the study. Six (4.1%) subjects discontinued from the study; 5 [3.4%] subjects due to withdrawal of consent and 1 [0.7%] subject due to a protocol violation (Subject 19/03 was randomized despite not meeting inclusion criteria).

TABLE 1

Subject Disposition, Screened Subjects

|  | Sequence F1/F2 (N = 76) | Sequence F2/F1 (N = 72) | Total (N = 148) |
|---|---|---|---|
| Screened [1] | 76 | 72 | 148 |
| Randomized [n (%)] | 76 (100.0) | 72 (100.0) | 148 (100.0) |
| Safety [n (%)] [2] | 76 (100.0) | 71 (98.6) | 147 (99.3) |
| Intent-to-treat Population [n (%)] [3] | 73 (96.1) | 71 (98.6) | 144 (97.3) |

TABLE 1-continued

Subject Disposition, Screened Subjects

|  | Sequence F1/F2 (N = 76) | Sequence F2/F1 (N = 72) | Total (N = 148) |
|---|---|---|---|
| Per Protocol Population [n (%)] [4] | 70 (92.1) | 69 (95.8) | 139 (93.9) |
| Completed Study [n (%)] | 73 (96.1) | 69 (95.8) | 142 (95.9) |
| Discontinued Study [n (%)] | 3 (3.9) | 3 (4.2) | 6 (4.1) |
| Primary Reason for Discontinuation [n (%)] |  |  |  |
| Protocol Violation/ non-compliance | 0 (0.0) | 1 (1.4) | 1 (0.7) |
| Other | 3 (3.9) | 2 (2.8) | 5 (3.4) |

F1 = 20 mg/1.0 ml formulation of GA;
F2 = 20 mg/0.5 ml formulation of GA;
GA = glatiramer acetate.
Note:
The number screened was used for the number randomized percentage. The number randomized was used as the denominator for all other percentages.
[1] Screened subjects refer to those subjects that were screened and had signed an informed consent.
[2] Safety population included all subjects that received at least one injection post screening.
[3] ITT population consisted of all randomized subjects with at least one post baseline observation, where baseline is considered to be the end of the period just prior to Period 1.
[4] Per Protocol population consisted of all subjects who completed both study periods with no major protocol deviations/violations.

Subject Demographics

Table 2 summarizes subject demographics for the safety population. Overall, the population was predominantly female (81.0%) and white (90.5%). The mean age of the population was 46.0 years with the range between 22 to 71 years. The subject groups receiving Sequence F1/F2 and Sequence F2/F1 were comparable in demographic characteristics.

TABLE 2

Subject Demographics, Safety Population

|  |  | Sequence F1/F2 (N = 76) | Sequence F2/F1 (N = 71) | Total (N = 147) |
|---|---|---|---|---|
| Age (years) | N | 76 | 71 | 147 |
|  | Mean | 45.1 | 46.9 | 46.0 |
|  | Standard Deviation | 10.64 | 9.64 | 10.17 |
|  | Median | 45.0 | 48.0 | 47.0 |
|  | Minimum, Maximum | 24, 71 | 22, 63 | 22, 71 |
| Gender [n (%)] | Male | 15 (19.7%) | 13 (18.3%) | 28 (19.0%) |
|  | Female | 61 (80.3%) | 58 (81.7%) | 119 (81.0%) |
| Race [n (%)] | Asian/Oriental | 0 (0.0%) | 1 (1.4%) | 1 (0.7%) |
|  | Black Or African American | 2 (2.6%) | 4 (5.6%) | 6 (4.1%) |
|  | White | 71 (93.4%) | 62 (87.3%) | 133 (90.5%) |
|  | Other | 3 (3.9%) | 4 (5.6%) | 7 (4.8%) |
| Weight (kg) | N | 76 | 71 | 147 |
|  | Mean | 85.6 | 77.4 | 81.6 |
|  | Standard Deviation | 20.07 | 20.82 | 20.78 |
|  | Median | 85.5 | 76.0 | 80.0 |
|  | Minimum, Maximum | 40, 137 | 48, 128 | 40, 137 |
| Height (cm) | N | 76 | 71 | 147 |
|  | Mean | 167.1 | 167.1 | 167.1 |
|  | Standard Deviation | 9.36 | 8.22 | 8.80 |
|  | Median | 165.0 | 166.1 | 165.0 |
|  | Minimum, Maximum | 150, 196 | 152, 191 | 150, 196 |

F1 = 20 mg/1.0 ml formulation of GA;
F2 = 20 mg/0.5 ml formulation of GA;
GA = glatiramer acetate Investigational Medicinal Products/Study Drugs
Treatments Administered GA injection is a clear, colorless to slightly yellow, sterile, non-pyrogenic solution for subcutaneous injection. It is supplied as a single-use PFS. The marketed medicinal product, Copaxone®, contains 20 mg GA and 40 mg mannitol in 1.0 ml of water for injection. The tested investigational medicinal product (IMP) contains 20 mg GA and 20 mg mannitol in 0.5 ml water for injection. GA is the name used to designate the active ingredient of Copaxone®. It is the acetate salt of a mixture of synthetic polypeptides composed of four amino acids: L-alanine, L-glutamic acid, L-lysine and L-tyrosine in a specified ratio and with an average molecular weight of 5,000-9000 Daltons.

Description of Investigational Medicinal Products/Study Drugs

Two concentrations of GA injection were used in this study:
  Formulation 1 (F1): 20 mg/1.0 ml of GA injection marketed as Copaxone®; and
  Formulation 2 (F2): 20 mg/0.5 ml of GA injection (F2).

Teva Pharmaceutical Industries Ltd., Israel, was responsible for the manufacturing of Copaxone®, according to Good Manufacturing Practice (GMP) principles and guidelines applicable to IMP.

Packaging, labeling, and distribution of study medication and supplies was performed by:
  Aptuit
  10245 Hickman Mills Drive
  Kansas City, Mo. 64137

The study drug was packed and shipped in appropriate storage boxes. Study drug was examined immediately upon arrival at the study center. If the drug supplies appeared to be damaged, the sponsor was contacted immediately. Individual subject's kit should not be open. The tamper proof seal should remain intact until the kit was open when providing the subject with study drug and instructions.

Each shipment of drug supplies for the study contained a shipment form to assist in maintaining current and accurate inventory records. When a shipment was received, the investigator/coordinator/pharmacist acknowledged receipt. Drug supplies must be kept in a secure, limited-access, refrigerated (2° C.-8° C.) and temperature-controlled storage area. Only authorized personnel had access to the study drug at the study centers.

The study drugs were dispensed to the subject at the study center by a person authorized by the study investigator at each scheduled visit. Instructions regarding study drug storage were provided to the subject. The subject returned all unused study drug at each visit. The investigator or designee was responsible for performing study drug accountability.

Method of Assigning Subjects to Treatment Groups

The subjects were randomly assigned in a 1:1 assignment ratio to one of two drug sequences; study drugs were distributed to the patient in the order of the sequence (F1/F2 or F2/F1). Block randomization stratified across study was done according to a computer generated schedule to ensure that subjects were distributed equally between the drug sequences.

Selection of Study Doses

The clinical use of GA in doses of 20 mg/ml (20 mg glatiramer acetate and 40 mg mannitol in 1.0 ml water for injection) once daily is indicated for reducing frequency of relapses in subjects with RRMS. However, injection-site reactions, including pain, were seen in clinical trials of GA to be the most frequent adverse reactions and were reported by the majority of subjects receiving GA. Therefore this study was designed to see if reducing injection volume would lead to a difference in pain associated with injections and injection-site reactions. Hence, the tested formulation contained 20 mg GA and 20 mg mannitol in 0.5 ml water for injection.

Selection of Timing and Dose for Each Subject

Subjects manually injected GA (F1 or F2) once daily for 14 days of treatment then crossover to the other formulation for another 14 days of treatment. There were no specific instructions regarding timing of dosing.

Prior and Concomitant Medications

All concomitant medications taken up to 30 days prior to screening were recorded.

Prior Medications:

Prior medications referred to any medication taken prior to the first injection of study medication. The following medications were not allowed 30 days prior to screening:
  immunomodulating therapies (IMT);
  corticosteroids by any route;
  investigational drugs or agents; and
  any other parenteral medications (e.g., IM, SC, IV, etc.)

Prior medications for the safety population are summarized in the Table 3 below. All randomized subjects had received prior medications. By design, all subjects were on glatiramer acetate (GA) prior to study entry. Patient 11/02 inadvertently had the end date of GA listed as the same day as the start of study drug resulting in GA not being listed as a prior medication but as a concomitant medication.

TABLE 3

Prior Medications, Safety Population

| Drug Class<br>Preferred Term [n (%)] | Sequence<br>F1/F2<br>(N = 76) | Sequence<br>F2/F1<br>(N = 71) | Total<br>(N = 147) |
| --- | --- | --- | --- |
| Any Prior Medication | 76 (100.0%) | 71 (100.0%) | 147 (100.0%) |
| Antibiotics | 0 (0.0%) | 1 (1.4%) | 1 (0.7%) |
| Clindamycin Hydrochloride | 0 (0.0%) | 1 (1.4%) | 1 (0.7%) |
| Centrally Acting Sympathomimetics | 1 (1.3%) | 0 (0.0%) | 1 (0.7%) |
| Methylphenidate Hydrochloride | 1 (1.3%) | 0 (0.0%) | 1 (0.7%) |
| Modafinil | 1 (1.3%) | 0 (0.0%) | 1 (0.7%) |
| Imidazole And Triazole Derivatives | 0 (0.0%) | 1 (1.4%) | 1 (0.7%) |
| Lotrisone | 0 (0.0%) | 1 (1.4%) | 1 (0.7%) |

TABLE 3-continued

| | Prior Medications, Safety Population | | |
|---|---|---|---|
| Drug Class<br>Preferred Term [n (%)] | Sequence<br>F1/F2<br>(N = 76) | Sequence<br>F2/F1<br>(N = 71) | Total<br>(N = 147) |
| Other Antiemetics | 0 (0.0%) | 1 (1.4%) | 1 (0.7%) |
| Promethazine | 0 (0.0%) | 1 (1.4%) | 1 (0.7%) |

F1 = 20 mg/1.0 ml formulation of GA;
F2 = 20 mg/0.5 ml formulation of GA
Note:
Prior medications were coded using the WHO Drug Dictionary (200809 version)
n = the number of subjects reporting medication use and the denominator for percentages is the safety population counts.
Note:
For Glatiramer Acetate, Patient 20-06 returned all study medication one day after screening and withdrew consent. Therefore this patient is not included in the count for prior use of glatiramer acetate as there is no stop date. 100% of patients were on Glatiramer Acetate (GA) prior to study entry. Patient 11-02 inadvertently had the end date of GA listed as the same day as the start of study drug resulting in GA not being listed as a prior medication but as a concomitant medication.

Concomitant Medications

Concomitant medications referred to any medication taken after the first injection of study medication, including those medications that started prior to entry into the study and continued into the study. All medications were allowed except for those medications listed below.

The following concomitant medications were not allowed during the study:
immunomodulating therapies (IMT);
corticosteroids by any route;
investigational drugs or agents; and
any other parenteral medications (e.g., IM, SC, IV, etc.)

Table 4 summarizes the concomitant medications used during the study by >5% of subjects in the safety population. The most frequently used drug classes were multivitamins (27.8% during use of each formulation), selective serotonin reuptake inhibitors (21.5% during 20 mg/1.0 ml GA and 22.9% during 20 mg/0.5 ml GA), other antidepressants (26.4% during 20 mg/1.0 ml GA and 25.7% during 20 mg/0.5 ml GA), benzodiazepine derivatives (21.2% during 20 mg/1.0 ml GA and 22.9% during 20 mg/0.5 ml GA), and propionic acid derivatives (21.5% during use of each formulation).

TABLE 4

| | Concomitant Medications (Used by >5% of Subjects), Safety Population | | |
|---|---|---|---|
| Drug Class<br>Preferred Term [n (%)] | Run-in Period<br>(N = 147) | 20 mg/1.0 ml GA<br>(N = 144) | 20 mg/0.5 ml GA<br>(N = 144) |
| Any Concomitant Medication | 144 (98.0%) | 141 (97.9%) | 141 (97.9%) |
| ACE Inhibitors, Plain | 13 (8.8%) | 12 (8.3%) | 12 (8.3%) |
| Lisinopril | 8 (5.4%) | 7 (4.9%) | 7 (4.9%) |
| Anilides | 18 (12.2%) | 19 (13.2%) | 20 (13.9%) |
| Paracetamol | 10 (6.8%) | 10 (6.9%) | 10 (6.9%) |
| Benzodiazepine Derivatives | 34 (23.1%) | 32 (22.2%) | 33 (22.9%) |
| Alprazolam | 12 (8.2%) | 12 (8.3%) | 12 (8.3%) |
| Clonazepam | 9 (6.1%) | 9 (6.3%) | 9 (6.3%) |
| Calcium | 22 (15.0%) | 22 (15.3%) | 22 (15.3%) |
| Calcium | 15 (10.2%) | 15 (10.4%) | 15 (10.4%) |
| Centrally Acting Sympathomimetics | 26 (17.7%) | 23 (16.0%) | 23 (16.0%) |
| Modafinil | 18 (12.2%) | 14 (9.7%) | 14 (9.7%) |
| Multivitamins, Other Combinations | 41 (27.9%) | 40 (27.8%) | 40 (27.8%) |
| Multivitamins | 41 (27.9%) | 40 (27.8%) | 40 (27.8%) |
| Other Analgesics And Antipyretics | 23 (15.6%) | 23 (16.0%) | 23 (16.0%) |
| Gabapentin | 23 (15.6%) | 23 (16.0%) | 23 (16.0%) |
| Other Antidepressants | 39 (26.5%) | 38 (26.4%) | 37 (25.7%) |
| Bupropion Hydrochloride | 10 (6.8%) | 10 (6.9%) | 10 (6.9%) |
| Duloxetine Hydrochloride | 13 (8.8%) | 13 (9.0%) | 12 (8.3%) |
| Other Antiepileptics | 22 (15.0%) | 20 (13.9%) | 20 (13.9%) |
| Topiramate | 8 (5.4%) | 7 (4.9%) | 7 (4.9%) |
| Other Centrally Acting Agents | 22 (15.0%) | 20 (13.9%) | 20 (13.9%) |
| Baclofen | 16 (10.9%) | 14 (9.7%) | 14 (9.7%) |
| Other Lipid Modifying Agents | 30 (20.4%) | 30 (20.8%) | 30 (20.8%) |
| Fish Oil | 26 (17.7%) | 26 (18.1%) | 26 (18.1%) |
| Platelet Aggregation Inhibitors Excluding Heparin | 24 (16.3%) | 22 (15.3%) | 22 (15.3%) |
| Acetylsalicylic Acid | 20 (13.6%) | 18 (12.5%) | 18 (12.5%) |
| Propionic Acid Derivatives | 32 (21.8%) | 31 (21.5%) | 31 (21.5%) |
| Ibuprofen | 27 (18.4%) | 26 (18.1%) | 26 (18.1%) |
| Selective Serotonin Reuptake Inhibitors | 33 (22.4%) | 31 (21.5%) | 33 (22.9%) |
| Fluoxetine | 11 (7.5%) | 11 (7.6%) | 11 (7.6%) |
| Thiazides, Plain | 8 (5.4%) | 9 (6.3%) | 9 (6.3%) |

TABLE 4-continued

Concomitant Medications (Used by >5% of Subjects), Safety Population

| Drug Class<br>Preferred Term [n (%)] | Run-in Period<br>(N = 147) | 20 mg/1.0 ml GA<br>(N = 144) | 20 mg/0.5 ml GA<br>(N = 144) |
|---|---|---|---|
| Hydrochlorothiazide | 8 (5.4%) | 9 (6.3%) | 9 (6.3%) |
| Thyroid Hormones | 18 (12.2%) | 18 (12.5%) | 18 (12.5%) |
| Levothyroxine Sodium | 12 (8.2%) | 12 (8.3%) | 12 (8.3%) |
| Vitamin D And Analogues | 27 (18.4%) | 27 (18.8%) | 28 (19.4%) |
| Ergocalciferol | 25 (17.0%) | 25 (17.4%) | 26 (18.1%) |

ACE = Angiotensin-Converting Enzyme;
GA = glatiramer acetate

Accountability and Compliance

Study drug accountability records were maintained at the site at all times. The identification number of the subject, the date, batch code, expiry date and quantity of study drug dispensed and the date and quantity of study drug returned by the subject were recorded. The returned study drug was noted on the appropriate inventory forms.

At study conclusion, all unused study drugs were returned to the sponsor or sponsor's designee for destruction. Documented evidence of destruction was made available to the site and the Clinical Management. Ancillary supplies did not have to be returned.

The subject was requested to return all unused study drug syringes in the original box to the study site at every visit. Compliance with the dosing regimen was determined by performing accountability of returned study drug. The number of returned syringes was counted and recorded by site personnel. The subject number, randomization number, quantity of study drug returned by the subject and visit date were recorded by the site personnel.

Compliance with the dosing regimen for each period was determined by performing accountability of returned unused study drug syringes. Compliance was computed as the actual number of used injections (dispensed minus returned) divided by the number of expected number of injections (number of days in the period) times 100 percent. Subjects with compliance 75% were considered compliant.

Medication compliance was quite high in this trial with the percentage of subjects showing 100% compliance equal to 94.4% following for 20 mg/0.5 ml dose and 91.7% following the 20 mg/1.0 ml dose of GA.

Study Conduct
Study Periods

Subjects were seen and evaluated in accordance with the following study evaluation schedule in Table 5.

TABLE 5

Evaluation Schedule

| | Screening and<br>Run-in Period[1]<br>(1 Week +<br>2 days) | Period 1<br>(2 weeks +<br>3 days) | Period 2<br>(2 weeks +<br>3 days) | End of study/<br>Early<br>Discontinuation |
|---|---|---|---|---|
| Study Procedure | Visit 1 | Visit 2 | Visit 3 | Visit 4 |
| Informed Consent[2] and Demography | X | | | |
| Medical History and Medication Use | X | | | |
| Eligibility Criteria | X | | | |
| Randomization | X | | | |
| Physical and Standard Neurological Examination | X | | | X |
| Vital signs[3], weight and height | X | X[4] | X[4] | X[4] |
| Laboratory Assessments[5] | X[6] | | X | X |
| Manual Injection Technique Training/Review | X | X | X | |
| Dispense/Review Diary | X | X | X | |
| Dispense Drug | X | X | X | |
| Study Injection Days | X[7] | X[7] | X[7] | |
| Subject Completes Diary | X | X | X | |
| Diary review/retrieval and drug accountability | | X | X | X |
| Record Concomitant Medications | X | X | X | X |
| Record AEs | | X | X | X |

[1]The start of the run in period was the day the first dose of study drug was taken. The run-in period was for seven days + 2 days.
[2]Consent occurred before the conduct of any study activities or evaluations
[3]Vital signs included: temperature, pulse, blood pressure
[4]Weight was collected at Visit 1 and Visit 4. Height was only collected at Visit 1 (Screening)
[5]Laboratory assessments included; hematology, clinical chemistry and urinalysis
[6]Included urine pregnancy test for women of childbearing potential
[7]If possible, the first injection of study drug for each treatment period was to be observed in the clinic, along with the review of the completed diary pages for the first day
Source: Appendix 16.1

Detailed Study Plan

Visit 1—Screening

Prior to performing any study activities/evaluations, the subject was thoroughly informed about all aspects of the study, including scheduled study visits and activities, and must sign the informed consent. A signed copy of the informed consent was given to the subject.

Screening procedures consisted of:

- Subjects signing the Institutional Review Board (IRB) approved written informed consent form before any study procedures were done.
- Assigning subject a study number.
- Obtaining and recording the subject's medical history, including documentation of the diagnosis of RRMS.
- Recording all medications used in the past 30 days, including those for MS. Record the indication, dose, dose administration schedule and start/stop date or ongoing.
- Recording vital signs (temperature, pulse, blood pressure), including height and weight.
- Completing physical examination, including: general appearance, skin, head, eyes, ears, nose and throat (HEENT), lungs, heart, abdomen, and musculoskeletal system.
- Completing standard neurological examination, to include the following: mental status, pupil and fundi, cranial nerves, motor examination, gait (if not wheelchair bound), coordination reflexes and sensory function.
- Drawing blood and collecting urine for clinical laboratory tests. Women of childbearing potential have a urine β-HCG to detect pregnancy. Pregnant women cannot be enrolled into the study.
- Instructing the subject on the following:
  - Manual injection technique. Subjects were instructed to continue using their normal process for preparing for an injection, such as use of ice or heat prior to or immediately after the injection. Site personnel explain the importance of being consistent in their injection technique for the next 5 weeks,
  - Seven day, seven site injection rotation (minimum of five site injection rotation), and
  - Diary completion.
- Randomizing subject to receive study drug for the run-in period. Randomization was determined according to a computer-generated randomization scheme. The lowest numbered study drug kit, available at the site was assigned as the randomization number to the subject. This information was recorded on a drug accountability log and in the CRF.
- Providing the subject with study drug (10 pre-filled syringes [PFS] of F1). Each subject was assigned the lowest numbered study drug kit available at the site.
- Providing the subject with the diary.
- If possible, observing the subject manually administering their first dose of study drug in the clinic and completion of their diary.
- Instructing the subject to contact the clinic in the event of any change in their medical condition, or the appearance of any AEs.
- Scheduling the subject to return to the clinic seven days from today's visit (+2 days) and to return his/her completed diary and unused study drug.

Visit 1 (screening) and first day of dosing for the Run-in Period could occur on the same day. If the first day of dosing could not be done during the screening visit, the first day of dosing must be done within two days of screening. The first day of dosing was captured in the CRF (run-in period).

Run-In Period:

The run-in period was seven (+two) days. Subjects were treated with F1 for the run-in period. The first day of the run-in period was the first day of dosing with study drug and continued for seven days. Run-in Period procedures for the subject consist of:

- Daily injection of study medication
- Daily completion of subject diary

Visit 2—Period 1:

Visit 2 occurred seven (+two) days after the date of first day of dosing in the run-in period.

Visit 2 procedures consisted of:

- Recording vital signs (temperature, pulse, blood pressure).
- Collecting and reviewing the completed diary with the subject. If any data points were missing, the instructions for completing the diary were reviewed with the subject.
- Reviewing with the subject their manual injection technique, and the seven site rotation.
- Recording any interruptions in study drug dosing. Counting and recording the number of unused syringes that were dispensed at Visit 1.
- Recording all concomitant medications and adverse events.
- Providing the subject with the study drug for Period 1 (20 PFS of F1 or F2).
- Providing the subject with the diary for Period 1.
- If possible, observing the subject manually administer their first dose of study drug, for Period 1, in the clinic and completion of their diary.
- Instructing the subject to contact the clinic in the event of any change in their medical condition, or the appearance of any AEs.
- Scheduling the subject to return to the clinic 14 days from today's visit (+three days) and to return his/her completed diary and unused study drug.

Period 1, (14 Days):

Period one (1) procedures for the subject consisted of:

- Daily study drug injections.
- Daily completion of subject diary.

Visit 3—Period 2:

Visit 3 occurred 14 (+three) days after Visit 2/Period 1 starts.

Visit 3 procedures consisted of:

- Recording vital signs (temperature, pulse, blood pressure).
- Collecting and reviewing the completed diary with the subject. If any data points were missing, the instructions for completing the diary were reviewed with the subject.
- Reviewing with the subject their manual injection technique, and the seven site rotation.
- Recording all concomitant medications and adverse events.
- Recording any interruptions in study drug dosing. Counting and recording the number of unused syringes that were dispensed at Visit 2.
- Providing the subject with the study drug for Period 2 (20 PFS of F1 or F2).
- Providing the subject with the diary for Period 2.
- If possible, observing the subject manually administering their first dose of study drug, for Period 2, in the clinic and completion of their diary.
- Instructing the subject to contact the clinic in the event of any change in their medical condition, or the appearance of any AEs.
- Drawing blood and collecting urine for clinical laboratory tests.

Scheduling the subject to return to the clinic 14 days from today's visit (+3 days) and to return his/her completed diary and unused study drug.

Period 2 (14 Days)

Period 2 procedures for the subject consisted of:
Daily study drug injections.
Daily subject diary completion.

Visit 4—End of Study or Early Discontinuation:

Visit 4 occurred 14 (+three) days after the start of Period 2 or at time of early discontinuation.

Visit 4/end of study or early discontinuation procedures consisted of:

Collecting and reviewing the completed diary with the subject.

Recording all concomitant medications and adverse events. If an AE was still ongoing, or a new AE was present at the end of study visit, it was followed until the medical condition returned to baseline or was considered stable or chronic and was recorded in the subject's source documents and in the CRF.

Recording vital signs (temperature, pulse, blood pressure), including weight.

Completing physical examination including: general appearance, skin, HEENT, lungs, heart, abdomen, and musculoskeletal system.

Completing standard neurological examination to include the following: mental status, pupil and fundi, cranial nerves, motor examination, gait (if not wheelchair bound), coordination, reflexes and sensory function.

Drawing blood and collecting urine for clinical laboratory tests.

Recording any interruptions in study drug dosing. Counting and recording the number of unused syringes that were dispensed at Visit 3.

Early discontinuation was defined as any withdrawal from the study prior to the completion of the full study period.

All reasons for discontinuation of therapy were documented in the source documents. If there were multiple reasons for early discontinuation, the primary reason for subject discontinuation was recorded in the CRF. If one of the reasons for early discontinuation was an AE, this was chosen as the reason. The sponsor was informed of all subjects who were withdrawn for this reason.

If a subject was withdrawn because of an adverse event, he/she was followed until the medical condition returned to baseline or was considered as stable or chronic.

Assessment Methods

Clinical Assessments

All study sites received instruction on how to train subjects to complete the daily diary, with particular emphasis on the VAS. This helped to ensure the standardization of the assessment.

Primary Outcome Measure:

The primary outcome measure was the difference in daily subject-reported injection pain occurring immediately after the injection for the two GA formulations as recorded on a 100 mm VAS, where 0 mm represents "no pain" and 100 mm represents "worst possible pain." The VAS was scored (i.e., measured) by four central raters. Inter-rater consistency was confirmed as follows; each of the four raters independently measured and scored each of the diary responses and recorded findings on a separate scoring sheet. Scorers provided responses in succession and submitted their scoring sheets to a designated team member in order to blind scores between scorers. Each score was subsequently listed and sent to a statistician for analysis. The overall agreement for all four raters based on Lin's Concordance Correlation Coefficient was 0.99988 with a 95% CI of (0.99977, 0.99995) and the average difference between rater pairs was 0.3 mm. The primary outcome was based on difference in total pain ratings between F1 and F2.

Secondary Outcome Measures:

The difference in daily subject-reported injection pain, occurring five minutes after the injection, for the two GA formulations as recorded on a 100 mm VAS where 0 mm represents "no pain" and 100 mm represents "worst possible pain". The VAS was scored (i.e., measured) by a single individual at a central location; daily scores across each period was averaged to provide total pain ratings. This secondary outcome was based on difference in total pain ratings between F1 and F2.

The difference in subject-reported presence or absence of LISRs and degree of severity scores that occurred within the five minute period following the injection, for the two formulations, as recorded daily on a 4-point ordinal scale where the response options are "none," "mild," "moderate," and "severe." Scores were recoded as "present" or "absent". LISRs to be assessed include: redness, itching, swelling, and lump. Daily scores across each period were averaged to provide two total LISR ratings: degree of severity and presence or absence of each LISR. These two total LISR ratings represent two endpoints for this secondary outcome measure.

The difference in subject-reported presence or absence of LISRs and degree of severity scores that occurred ("at its worst") within the previous 24 hours, for the two formulations as recorded daily on a 4-point ordinal scale where the response options are "none," "mild," "moderate," and "severe." Scores were recoded as "present" or "absent." LISRs assessed include: redness, itching, swelling, and lump. Daily scores across each period were averaged to provide two total LISR ratings: degree of severity and presence or absence of each LISR. These two total LISR ratings represent two endpoints for this secondary outcome measure.

Exploratory Outcome Measures:

The average pain presence scores immediately and at 5 minutes post injection by study drug formulation. Pain scores were dichotomized as either No Pain=0 (a VAS score of 0-4 mm), or Pain=1 (a VAS score of 5-100 mm). The pain presence score was averaged across the period for each subject for both the immediate and 5-minute pain recordings.

The average 5-minute and 24-hour total LISR scores and daily 5-minute and 24 hour scores for each individual LISR symptom by drug formulation.

The number of subjects reporting no symptoms at 5 minutes and 24 hours post-injection summarized for the following day intervals: 0-3, 4-6, 7-9, and >9, by drug formulation.

The frequency of subjects reporting symptoms at each injection site summarized by symptom type and drug formulation.

Safety Assessment

Adverse events were recorded as soon as the subject signed the Informed Consent Form and throughout the study. Adverse events were reviewed and updated at each subsequent visit and during any phone contact with the subject.

Adverse Event:

An adverse event (AE) was defined as any untoward medical occurrence in a clinical study subject administered a medicinal product and which does not necessarily have a causal relationship with the treatment.

In the study, any event occurring after the clinical study subject has signed the study Informed Consent was recorded and reported as an AE. An adverse event could therefore be any unfavorable and unintended sign (including an abnormal laboratory finding), symptom, or disease temporally associated with the use of an investigational medicinal product, whether or not considered related to the investigational medicinal product.

A new condition or the worsening of a pre-existing condition was considered an AE. Stable chronic conditions such as arthritis that were present prior to study entry and do not worsen during the study were not considered AEs. Worsening of the disease under study was measured by clinical impression of the Investigator and was only recorded as an AE if the outcome was more serious than would normally be expected from the normal course of the disease in a particular subject.

An abnormal result of diagnostic procedures including abnormal laboratory findings was considered an AE if it:
resulted in subject's withdrawal by the investigator;
was associated with a serious adverse event (SAE);
was associated with clinical signs or symptoms;
was considered by the physician to be of clinical significance.

The intensity or severity of the AE were characterized as:
Mild: AE which is easily tolerated.
Moderate: AE sufficiently discomforting to interfere with daily activity.
Severe: AE which prevents normal daily activities.

Unlabeled/Unexpected AE:
A reaction which was not included in the Adverse Reaction section of the relevant Reference Safety Information by its specificity, severity, outcome or frequency.

The relationship of an AE to the study drug is characterized according to Table 6 below.

A determination of the relationship (if any) between an AE and the study drug was made. A causal relationship was present if a determination was made that there was a reasonable possibility that the AE could have been caused by the drug.

AEs were recorded as soon as the subject signed the ICF and throughout the study. AEs were to be reviewed and updated at each subsequent visit and during any phone contact with the subject.

Any injection site reaction not captured in the diary (i.e. anything other than redness, itching, lump, swelling or pain) but reported by the subjects was captured as an AE and followed until resolution. If the subject reported one of the events mentioned in the diary, but the Primary Investigator and/or the subject felt that there was something unusual about it compared to their usual injection site reaction, this too was reported as an AE.

With regard to reported AEs, the following were recorded:
date of onset,
description of the AE,
severity,
seriousness,
action taken,
relationship to the study drug,
outcome of the event, and
date of resolution.

Serious Adverse Event:
A Serious Adverse Event (SAE) is defined as an event which
was fatal
was life-threatening at the time of event
resulted in persistent or significant disability/incapacity
constituted a congenital anomaly/birth defect

TABLE 6

Classification of AEs With Respect to Study Drug

| TERM | DEFINITION | CLARIFICATION |
| --- | --- | --- |
| No Reasonable Possibility | This category applies to those adverse events which, after careful consideration, are clearly due to extraneous causes (disease, environment, etc.) or to those adverse events, which after careful medical consideration at the time they are evaluated, are judged to be unrelated to the test drug. | An adverse experience may be considered No Reasonable Possibility if it is clearly due to extraneous causes or when (must have two): It does not follow a reasonable temporal sequence from the administration of the test drug. It could readily have been produced by the subject's clinical state, environmental or toxic factors, or other modes of therapy administered to the subject. It does not follow a known pattern of response to the test drug. It does not reappear or worsen when the drug is re-administered. |
| Reasonable Possibility | This category applies to those adverse events for which, after careful medical consideration at the time they are evaluated, a connection with the test drug administration cannot be ruled out with certainty or felt with a high degree of certainty to be related to the test drug. | An adverse experience may be considered possibly related if or when (at least two of the following): It follows a reasonable temporal sequence from administration of the drug. It could not be reasonably explained by the known characteristics of the subject's clinical state, environmental or toxic factors or other modes of therapy administered to the subject It disappears or decreases on cessation or reduction in dose. There are important exceptions when an adverse event does not disappear upon discontinuation of the drug, yet drug-relatedness clearly exists. It follows a known pattern of response to the test drug. | required inpatient hospitalization or prolongation of existing hospitalization for treatment of AE, or occurred as a consequence of the AE, unless hospitalization was for:
IV steroid treatment of a relapse, unless it was a worsening of condition beyond expected disease progression
elective or pre-planned treatment for a pre-existing condition that had not worsened since the start of study drug
was medically important, i.e., defined as an event that may not have been immediately life-threatening but jeopardized the subject or may have required medical or surgical intervention to prevent one of the outcomes listed above.

Important medical events were those which may not have been immediately life-threatening, but may have jeopardized the subject and may have required intervention to prevent one of the other serious outcomes listed above. Events such as intensive treatment in an emergency room or at home for allergic bronchospasm; blood dyscrasias or convulsions that do not result in hospitalization, resulting in an adverse event are normally considered serious by this criterion.

Inpatient hospitalization or prolongation of existing hospitalization means that hospital inpatient admission and/or prolongation of hospital stay were required for treatment of AE, or that they occurred as a consequence of the event. It does not refer to pre-planned elective hospital admission for treatment of a preexisting condition that has not significantly worsened, or to diagnostic procedure. It does not refer either to hospitalization for I.V. steroid treatment of a relapse, unless it was a worsening of condition beyond expected disease progression.

All pregnancies, including normal pregnancies without an AE, were to be reported to the CRO for inclusions to the safety database. Pregnancies were to be followed up to determine outcome, including spontaneous or voluntary termination, details of birth, presence, or absence of any birth defect, congenital abnormalities, or maternal and newborn complications.

Pregnancy report forms and pregnancy follow-up forms were to be provided by the CRO. The pregnancies reporting procedure was the same as SAE reporting procedure.

The term "life-threatening" in the definition of "serious" refers to an event in which the patient was at risk of death at the time of the event; it does not refer to an event which hypothetically might have caused death if it were more severe. Any new SAE that occurs after the study period and is considered to be related (possibly/probably) to the IMP or study participation should be recorded and reported immediately. The study period for the purpose of SAE reporting is defined as the period from the subject's signature on the informed consent form until 30 days after the last dose.

Safety Laboratory Evaluations:
All laboratory testing, except the urine pregnancy test, was performed by:
Physicians Reference Laboratory (PRL)
7800 West 110$^{th}$ Street
Overland Park, Kans. 66210
The following tests are performed at Visit 1 (screening), Visit 3, and Visit 4/End of Study.
Serum Chemistry:
Glucose, creatinine, total bilirubin, BUN, AST(SGOT), ALT(SGPT), cholesterol, total protein, albumin, sodium, potassium, chloride, calcium and phosphorous.

Hematology:
Red blood cells (RBC) count, hemoglobin, hematocrit, white blood cells (WBC) count and differential count (reported in %) and platelet count.
Urinalysis dipstick:
Color, clarity, specific gravity, pH, protein, glucose, ketones, leukocyte esterase, nitrite, bilirubin, urobilinogen and blood.
Urine β-HCG pregnancy test was to be performed at Visit 1 (screening) for women of childbearing potential.
Vital Signs:
Vital signs, including body temperature, pulse and blood pressure were completed at all scheduled visits. Height and weight were measured at screening and weight was measured only at the end of the study.
Physical Examination:
A physical examination, including general appearance, skin, HEENT, lungs, heart, abdomen, and musculoskeletal systems, was performed and documented by the investigator or a qualified designee on Visit 1 (screening), and Visit 4 (end of study).
Any abnormal findings, assessed by the investigator as clinically significant, were recorded in the relevant CRF modules (e.g. adverse event, medical history).
Standard Neurological Examination:
A standard neurological examination was performed and documented by the investigator or a qualified designee on Visit 1 (screening), and Visit 4 (end of study). Examinations included mental status, pupil and fundi, cranial nerves, motor examination, gait (if not wheelchair bound), coordination, reflexes and sensory function.
Any abnormal findings, assessed by the investigator as clinically significant, were recorded in the relevant CRF modules (e.g. adverse event, medical history).
Statistical Methodology
This study compared the tolerability and safety of two formulations of GA for SC injection; 20 mg/1.0 ml (F1) or 20 mg/0.5 ml (F2).
Statistical and Analytical Methods
All descriptive and inferential statistical analyses planned were performed using SAS® (SAS Institute Inc., Cary, N.C.), Version 8. Statistical tests were 2-tailed unless otherwise stated and statistical significance was declared, if the p-value was ≤0.05 without adjustment for multiple testing. Nominal p-values are presented for hypothesis testing and were displayed to 3 decimal places.
Descriptive statistics for continuous variables consisted of N, mean, median, standard deviation (SD), minimum, and maximum values. For categorical variables, the number and percent (%) of each category are displayed.
Baseline was defined as the last assessment prior to the first injection of study medication. For clinical outcomes analyses, baseline was any measurement just prior to starting the Period 1 study treatment. For safety, baseline was defined as the measurements assessed just prior to starting the run-in period treatment (non-missing screening visit).
Data Sets Analyzed:
Data from this study were summarized and analyzed for the 3 analysis populations, namely the Safety population, the Intent-To-Treat (ITT) population, and the Per Protocol (PP) population, defined as follows:
Safety population: The safety population (n=147) consists of all subjects that received at least one injection of either formulation.
Intent-to-Treat population (ITT): Consists of all randomized subjects with at least one post baseline observation, where baseline was considered to be the end of the run-in period just prior to Period 1 (n=144).

Per Protocol population (PP): Consists of all subjects who complete both study treatment periods with no major protocol deviations/violations. This population was determined prior to unblinding (n=139).

"Screened subjects" refers to those subjects that signed an informed consent and had screening assessments.

All the primary and secondary efficacy analyses were done for the ITT population and the PP population. All the safety analyses were done for the safety population.

Subject Demographic and Baseline Characteristics:

Demographics and background variables included age, gender, race, height, and weight and were summarized using descriptive statistics. Age was calculated as the integer portion of the date of the screening visit minus the date of birth, divided by 365.25 days per year. Height and weight are presented in cm and kg.

The disposition of all randomized subjects was summarized by treatment sequence and total subjects in Table 1. The number and percentage of subjects included in each study population is presented. The number and percentage of subjects who completed or withdrew from the study are also presented. For subjects who withdrew from the study prematurely, reasons for withdrawal were summarized.

Protocol violations/deviations identified by the monitors and data management were discussed prior to data freeze. A review of the data including, but not limited to, inclusion/exclusion criteria, drug and diary compliance, and prohibited medications to exclude subjects from the PP population was made by the sponsor prior to data freeze. Unless a documented decision of protocol violations/deviations inclusion was made, no subjects were allowed to be removed from statistical summaries.

Exposure was defined as duration of treatment and was calculated for the run-in period as well as from Day 1 (the day of first dose for each period) to the last dose of each period. Total exposure was the summation of the exposure from both periods, summarized descriptively and by drug formulation.

Frequency and percentages was used to summarize concomitant and prior medication groups for the safety population. Medications were coded using the World Health Organization Drug Dictionary (WHODD), Version 2008. Subjects with multiple occurrences of a medication were counted only once.

Medical history was obtained from each subject and listed by drug formulation sequence group.

Handling of Dropouts or Missing Data:

In general, data were summarized and analyzed "as observed" without imputation. A sensitivity analysis was performed to confirm the "as observed" analysis as follows:

A LOCF approach was used to impute data for all post-baseline time points with missing data within a period for Periods 1 and 2, for the primary clinical outcome variable. Baseline values were not carried forward.

Multicenter Studies:

All study sites were pooled together because subject randomization was based on many sites with most sites enrolling 6 to 12 subjects. Subjects were randomized in blocks according to a computer-generated schedule to ensure that subjects were distributed equally between the drug sequences.

Given the number of investigator sites (23 sites that were eligible to enroll, 21 sites enrolled at least one subject) relative to the number of enrolled subjects (N=148), stratification of summarization and analyses by site was not planned (and thus, the pooling of small investigator sites was not applicable).

Primary Clinical Outcomes Variable:

The primary clinical outcomes variable was the total injection pain rating occurring immediately after injection (i.e., Immediate Total Pain score). The null hypothesis was that there was no difference between the 2 study drug formulations.

The primary analysis for testing the Immediate Total Pain score was based on the analysis of variance (ANOVA) model for a 2-treatment crossover study with treatment, sequence, and period as fixed effect terms, and a random effect term of subject within sequence. The corresponding 95% confidence interval for the treatment difference in scores is presented.

Secondary Clinical Outcomes Variables:

Clinical outcomes were also assessed by the following secondary variables:

Difference between the two study drug formulations in total injection pain rating occurring five minutes after the injection between the two study drug formulations.

Difference between the two study drug formulations in total injection LISR severity rating occurring within the five minute period after the injection between the two study-drug formulations.

Difference between the two study drug formulations in total injection LISR occurrence (i.e., presence) within the five minute period after the injection between the two study drug formulations Difference between the two study drug formulations in total injection LISR severity rating occurring within the previous 24 hours after the injection between the two study-drug formulations.

Difference between the two study drug formulations in total injection LISR occurrence (i.e., presence) within the previous 24 hours after the injection between the two study drug formulations.

In addition to summaries using descriptive statistics for all clinical outcomes variables, secondary variables were analyzed using the ANOVA technique described above for the primary clinical outcomes variable analysis. Since the primary outcomes variable was not normally distributed, the same non-parametric method was employed for the secondary clinical outcomes variables. If required, appropriate categorical analysis procedures were performed. Plots are provided for visual representation of the daily pain scores and the presences/absence and severity of LIRSs, by study drug formulation.

Exploratory Analysis:

Average Immediate Pain Presence Total scores by study drug formulation.

Average 5-minute Pain Presence Total scores by study drug formulation.

Average 5-minute daily scores for each individual LISR symptom by drug formulation. Plots of mean daily scores are also provided in FIGS. 4(A-D).

Average 24-hour daily scores for each individual LISR symptom by drug formulation. Plots of mean daily scores are also provided in FIG. 5(A-D).

Tolerability Analyses:

Tolerability was based on between group comparisons in subjects prematurely discontinuing the study due to AEs, injection site pain or reactions, and laboratory abnormalities. In addition, if the data warranted, the Kaplan-Meier product-limit algorithm was applied to compute the time to discontinuation curves, the median event time, and the 95% confidence interval for the median for each study drug formulation.

Safety Analyses:

All safety analyses and summaries were performed using the safety population and included AEs, clinical laboratory tests, physical and neurological examinations, and vital signs assessments. The baseline assessment for all safety parameters was the screening assessment.

Adverse Events:

AEs were classified by system organ class (SOC) and preferred term using the Medical Dictionary for Regulatory Affairs (MedDRA) dictionary version 11.1 and the incidence summarized by study drug formulation. The incidence of subjects with AEs, study drug related AEs and SAEs (if any) were summarized by study drug formulation according to preferred term and SOC for all treatment emergent adverse events (TEAEs). TEAEs were assigned to the drug formulation received during the Period that they occurred (including run-in). In addition, the most frequently occurring TEAEs, occurring in at least 5% in either study drug formulation are presented by SOC and preferred term by study drug formulation.

A treatment-related AE was defined as an AE considered possibly or probably related to the study drug by an investigator. The most severe occurrence of each preferred term and the most related occurrence of each preferred term were selected for each subject.

Any AE starting at Screening was not recorded on the AE page, but instead was added to the medical history.

Clinical Laboratory Tests:

Clinical laboratory assessments, including tests from hematology and chemistry were summarized using descriptive statistics, by study drug formulation at baseline (Screening) and at each assessment time point, including change from baseline, during the study.

Vital Signs:

Vital signs, including blood pressure, pulse rate, and temperature were summarized using descriptive statistics, by study drug formulation at baseline and at each assessment time point, including change from baseline, during the study Physical Examinations:

The count and percentage of physical examination changes from baseline were summarized for: general appearance, skin, head, eyes, ears, nose and throat (HEENT), lungs, heart, abdomen, musculoskeletal system.

Neurological Examinations:

Neurological examination changes from baseline were summarized in a shift table for: mental status, pupil and fundi, cranial nerves, motor examination, gait (if not wheelchair bound), coordination reflexes and sensory function.

Sample Size Rationale:

In a previous study (PM020) in subjects using an Autoject®2 for glass syringe device for administering 20 mg/1.0 ml dose of Copaxone®, the mean and standard deviation for the pain ratings averaged over a 4-day period immediately following the daily injection was used to estimate the sample size for this study. This study averages injections over a 14-day period. Using the mean of 1.69 and standard deviation of 0.81 from the PM020 study, an effect size of 18%, and a two-tailed t-test for correlated sample means with and alpha value of 0.05 and 80% power, approximately 60 subjects per drug sequence group (120 in total) are required. Allowing for a 10% dropout rate, then a total of at least 132 patients were needed for the study.

Randomization:

After a subject meets the eligibility criteria, he/she was allocated to a treatment sequence, based on a randomization procedure employing a 1:1 assignment ratio, with blocks stratified by center. The randomization scheme was prepared by the CRO.

Once the enrollment of a subject was approved, a subject ID number (subject number) was assigned.

Results

Measurements of Treatment Compliance

Overall, 99.56% of subjects were compliant during the 20 mg/1.0 ml dose of GA and 99.46% of subjects were compliant during the use of 20 mg/0.5 ml dose of GA. The percentage of subjects showing 100% compliance was little higher during the 20 mg/0.5 ml dose (94.4%) than during the 20 mg/1.0 ml dose (91.7%) of GA. One subject (16/06) receiving 20 mg/1.0 ml dose of GA had >100% (106%) compliance doe to mistakenly taking an injection on the morning of the Visit 4 appointment; however, this was not considered an overdose.

Primary Clinical Outcome Measure

Table 7 presents the analysis of average immediate VAS total pain scores for the ITT population. The mean immediate VAS total pain score was 11.89 after administration of 20 mg/1.0 ml dose of GA and was 8.64 after administration of 20 mg/0.5 ml dose of GA. This indicates that less pain was experienced after 20 mg/0.5 ml injection of GA compared with 20 mg/1.0 ml injection of GA.

In comparing the 2 treatments, the ranked VAS scores differed by 21.1 (95% CI: 13.4, 28.8) observations; this difference in the ranks was statistically significant (p<0.0001) in favor of 20 mg/0.5 ml dose of GA, although neither group had a high level of pain on average as the VAS scale ranges from 0 to 100.

TABLE 7

Analysis of Average Immediate VAS Total Scores, ITT Population

| | | 20 mg/1.0 ml GA (N = 144) | 20 mg/0.5 ml GA (N = 144) | P-value [a] |
|---|---|---|---|---|
| VAS - | N | 143 | 144 | |
| Immediate | Mean | 11.89 | 8.64 | |
| Scores | Standard Deviation | 14.375 | 10.825 | |
| | Median | 6.29 | 4.69 | |
| | Minimum, Maximum | (0.7, 73.3) | (0.7, 72.1) | |
| | Least Square Mean [a] | 154.7 | 133.6 | Period: 0.9261 |
| | 95% CI | (141.0, 168.3) | (120.0, 147.2) | Sequence: 0.6271 |
| | | | | Treatment: <0.0001 |

TABLE 7-continued

Analysis of Average Immediate VAS Total Scores, ITT Population

| | 20 mg/1.0 ml GA (N = 144) | 20 mg/0.5 ml GA (N = 144) | P-value [a] |
|---|---|---|---|
| Comparison F1 to F2 [b] | | | |
| Difference in LS Means [a] | 21.1 | | |
| 95% CI for Difference | (13.4, 28.8) | | |
| P-value | <0.0001 | | |

F1 = 20 mg/1.0 ml formulation of GA;
F2 = 20 mg/0.5 ml formulation of GA;
GA = glatiramer acetate;
ITT = Intent-to-treat;
LS Means = least square means
[a] ANOVA model with mean ranked average VAS score as the response; sequence, period, and treatment as fixed effects and subject within sequence as random effect. Ranked data was used due to non-normality.
[b] Comparison of the 20 mg/1.0 ml GA drug formulation to the 20 mg/0.5 ml GA drug formulation.

FIG. 1 presents the plot of daily total immediate VAS total scores for the ITT population.

A sensitivity analysis of average immediate VAS total scores using last observation carried forward (LOCF) for subjects discontinuing early in the ITT population was performed. Similar results were observed in this sensitivity analysis with statistically significant difference (p<0.0001) between the two formulations of GA in favor of 20 mg/0.5 ml dose.

Figure 2:
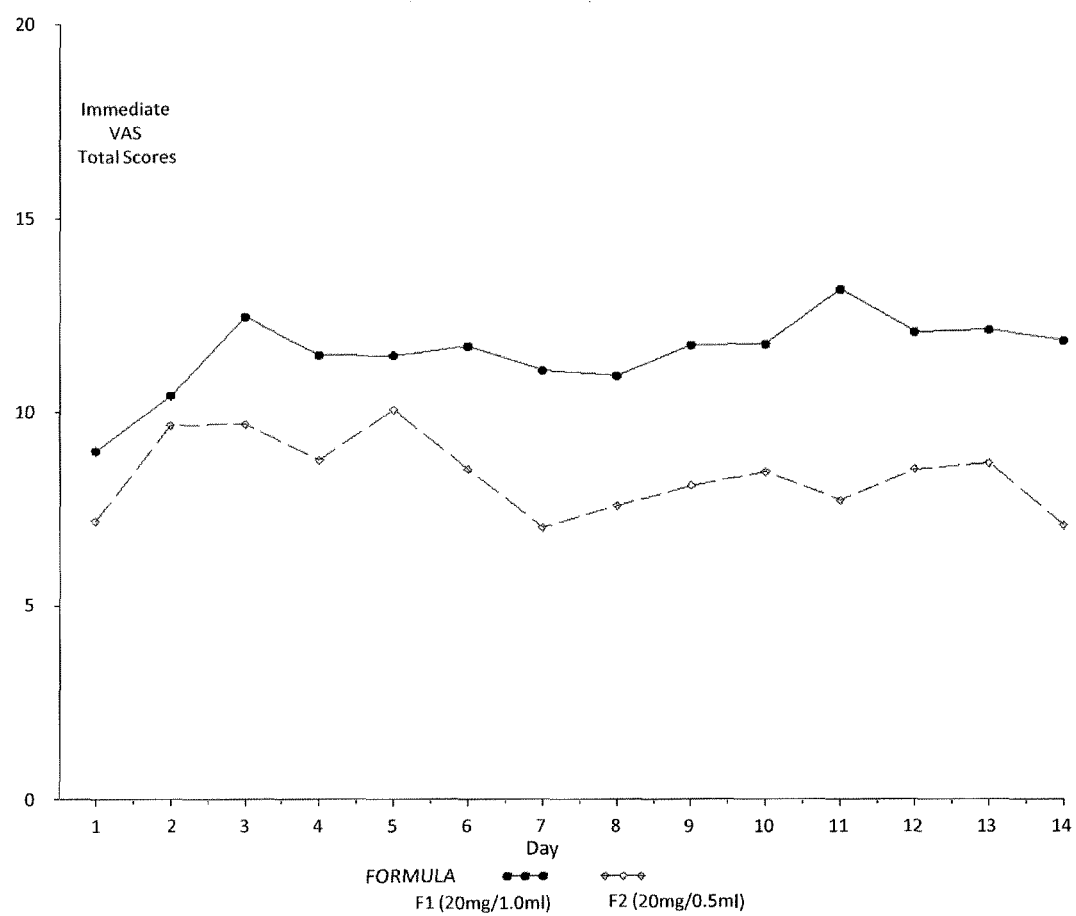

The analysis of average immediate VAS total scores for the PP population was also performed. The mean immediate VAS total score for the PP population was 11.44 after administration of 20 mg/1.0 ml dose of GA and was 8.31 after administration of 20 mg/0.5 ml dose of GA. In the comparison of the two treatments, the ranked VAS scores differed by 20.4 (95% CI: 12.7, 28.0) observations; this difference in the ranks was statistically significant (p<0.0001) in favor of 20 mg/0.5 ml dose of GA The plot of daily total immediate VAS total scores for the PP population is presented in FIG. 2. In comparison to the ITT population, similar results were observed in the PP population with statistically significant difference (p<0.0001) in the 2 formulations of GA in favor of 20 mg/0.5 ml dose of GA.

Secondary Clinical Outcome Measures

Five-Minute Total Pain Score

Table 8 presents the analysis of average 5-minute VAS total scores for the ITT population. The mean VAS total pain score was 17.19 at 5 minutes after administration of 20 mg/1.0 ml dose of GA and was 11.85 at 5 minutes after administration of 20 mg/0.5 ml dose of GA. In the comparison of the 2 treatments, the ranked VAS scores differed by 27.2 (95% CI: 20.2, 34.3) observations; this difference in the ranks was statistically significant (p<0.0001) in favor of 20 mg/0.5 ml dose of GA.

Figure 3:
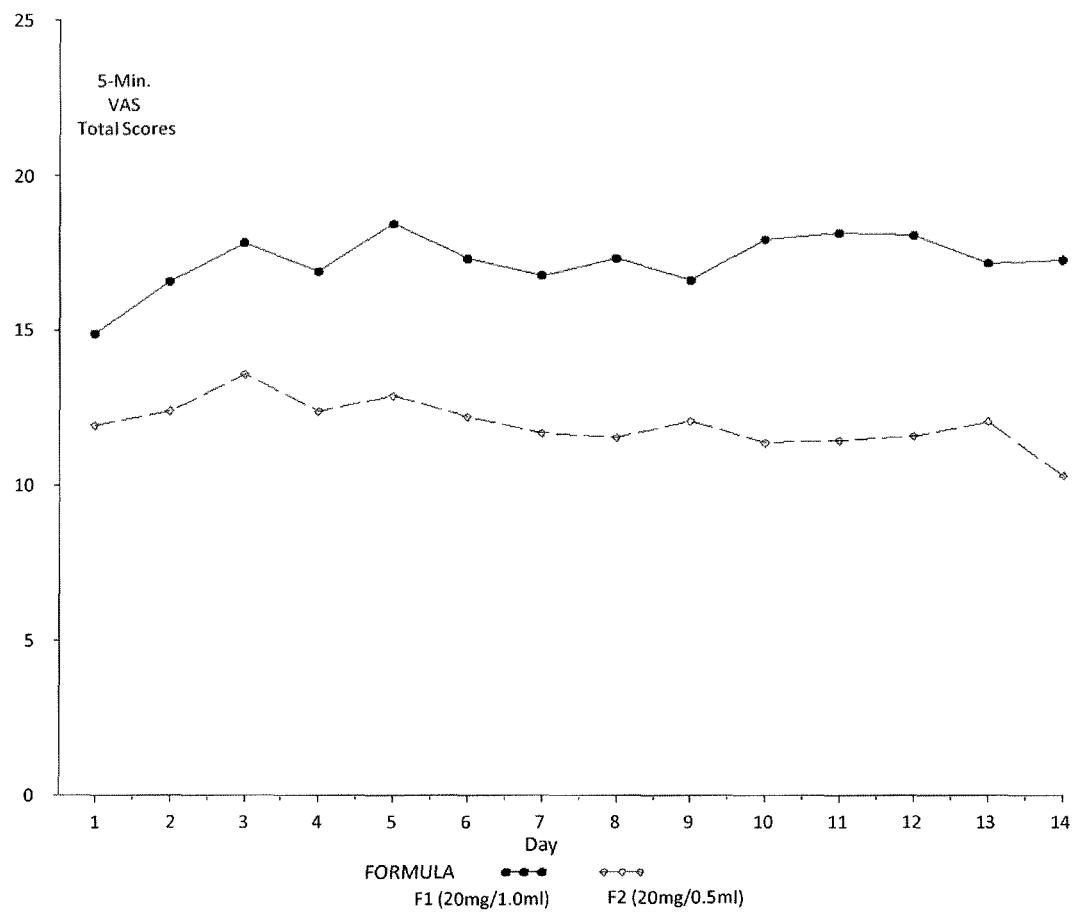
FIG. 3.
Plot of daily total 5-minute VAS total scores for the ITT population.
Figure 4A:
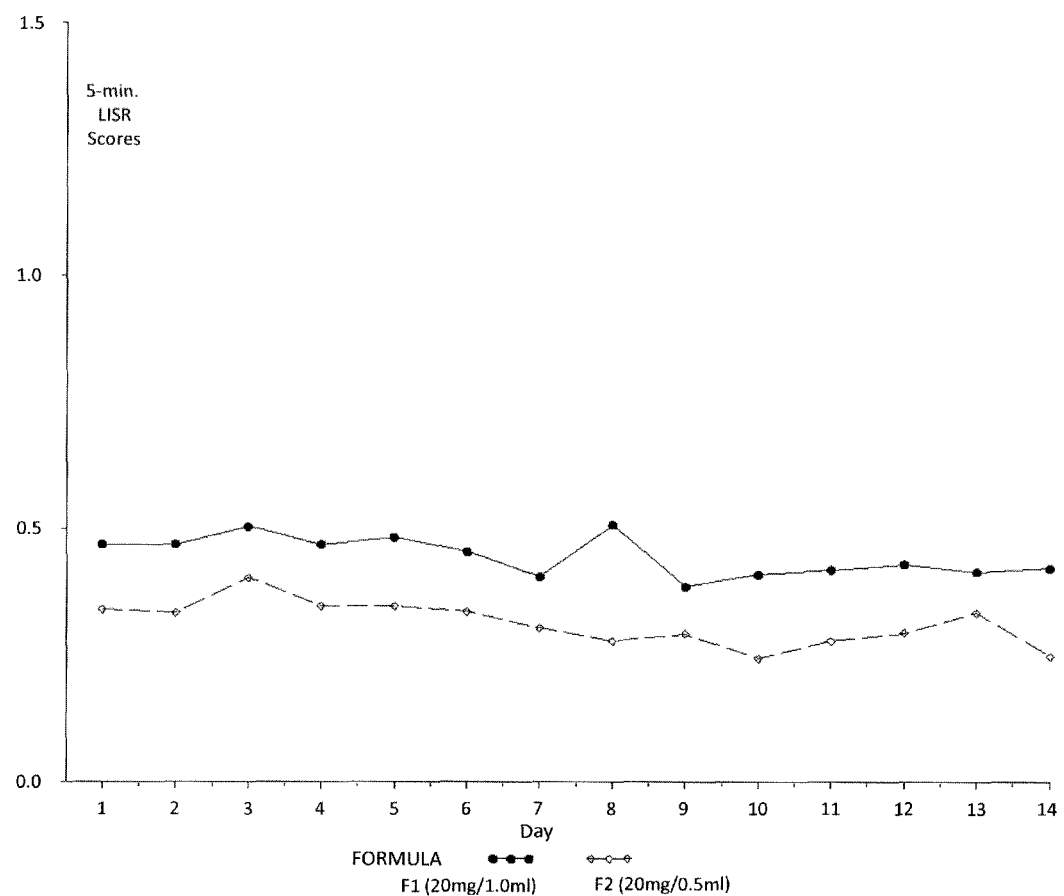
FIGS. 4 (A-D).
Plots of average daily 5-minute LISR scores for the ITT population; swelling (A), redness (B), itching (C) and lump (D) were the 4 symptoms considered as LISRs during the study.
Figure 4B:
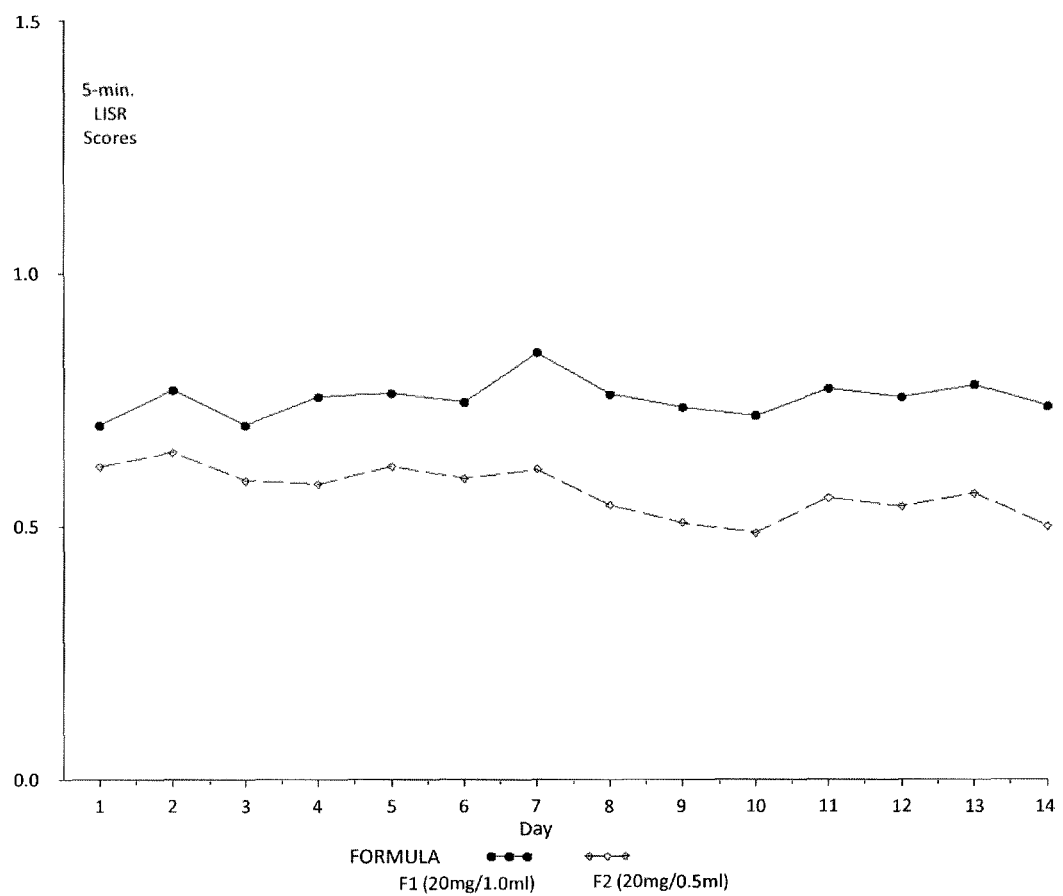
Figure 4C:
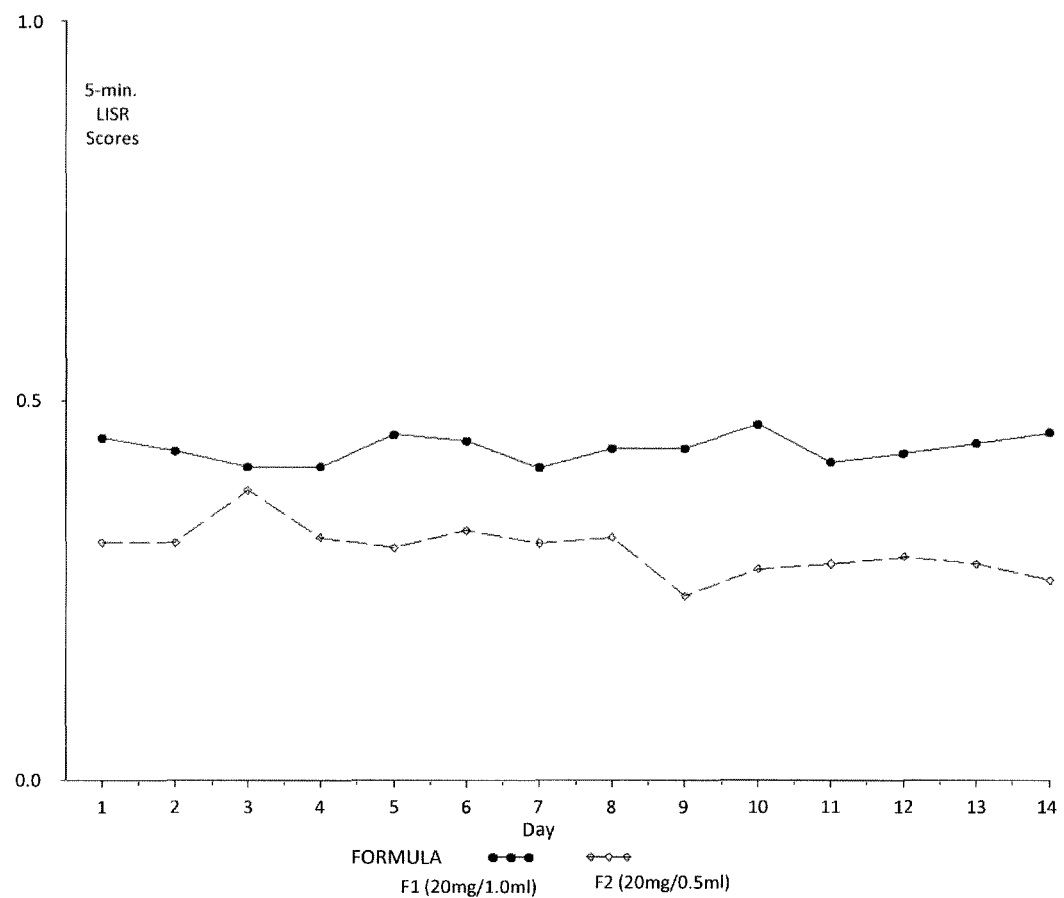
Figure 4D:
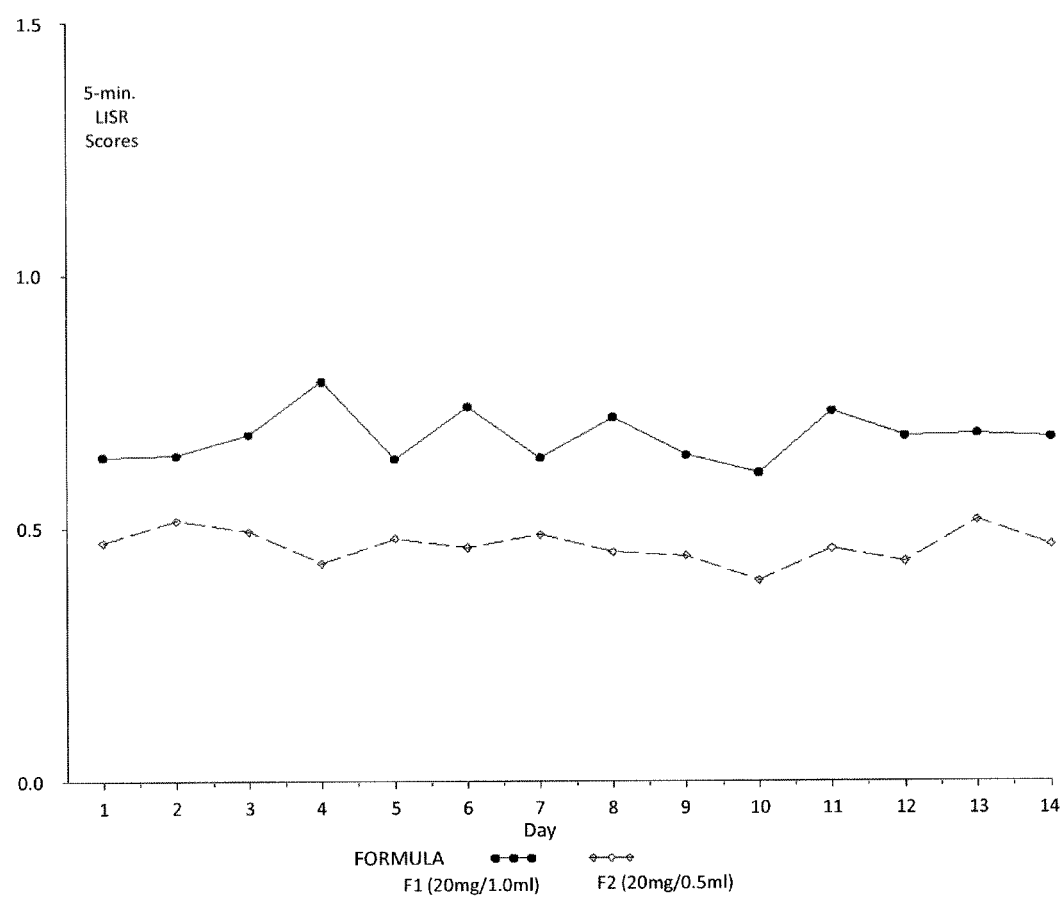
Figure 5A:
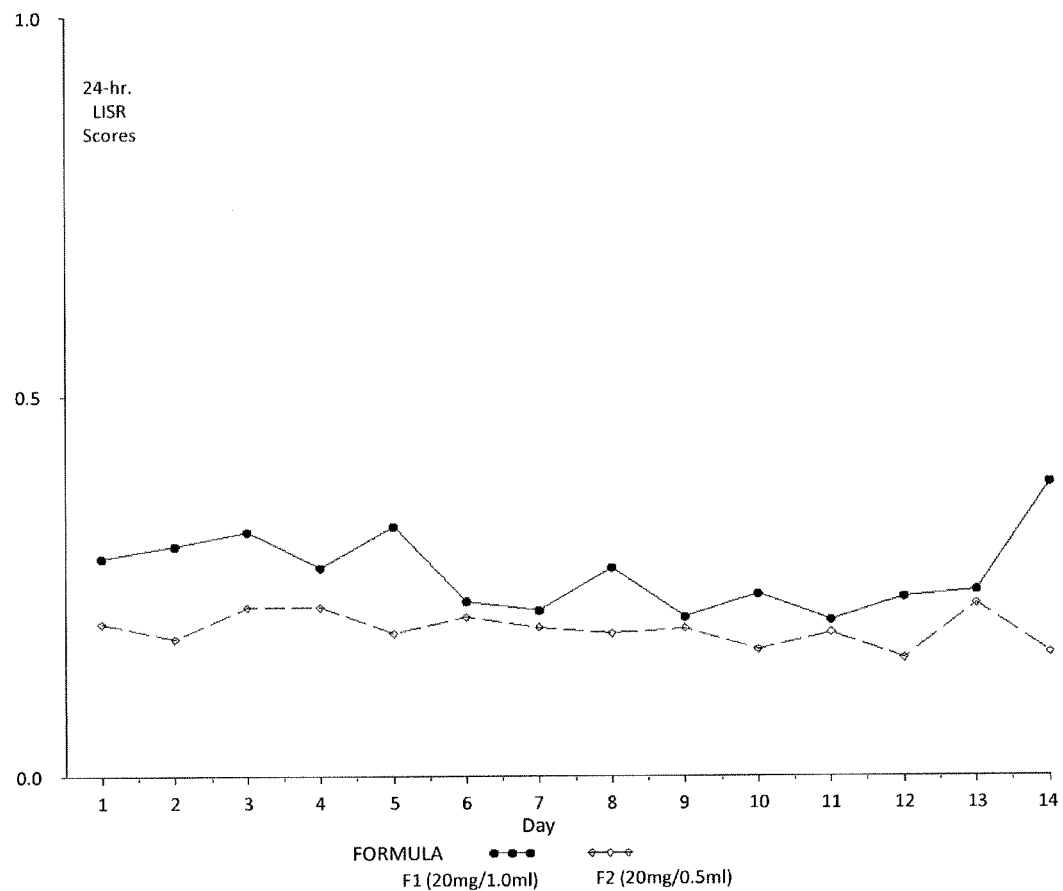
FIGS. 5 (A-D).
Plots of average daily 24-hour LISR scores for the ITT population; swelling (A), redness (B), itching (C) and lump (D) were the 4 symptoms considered as LISRs during the study.
Figure 5B:
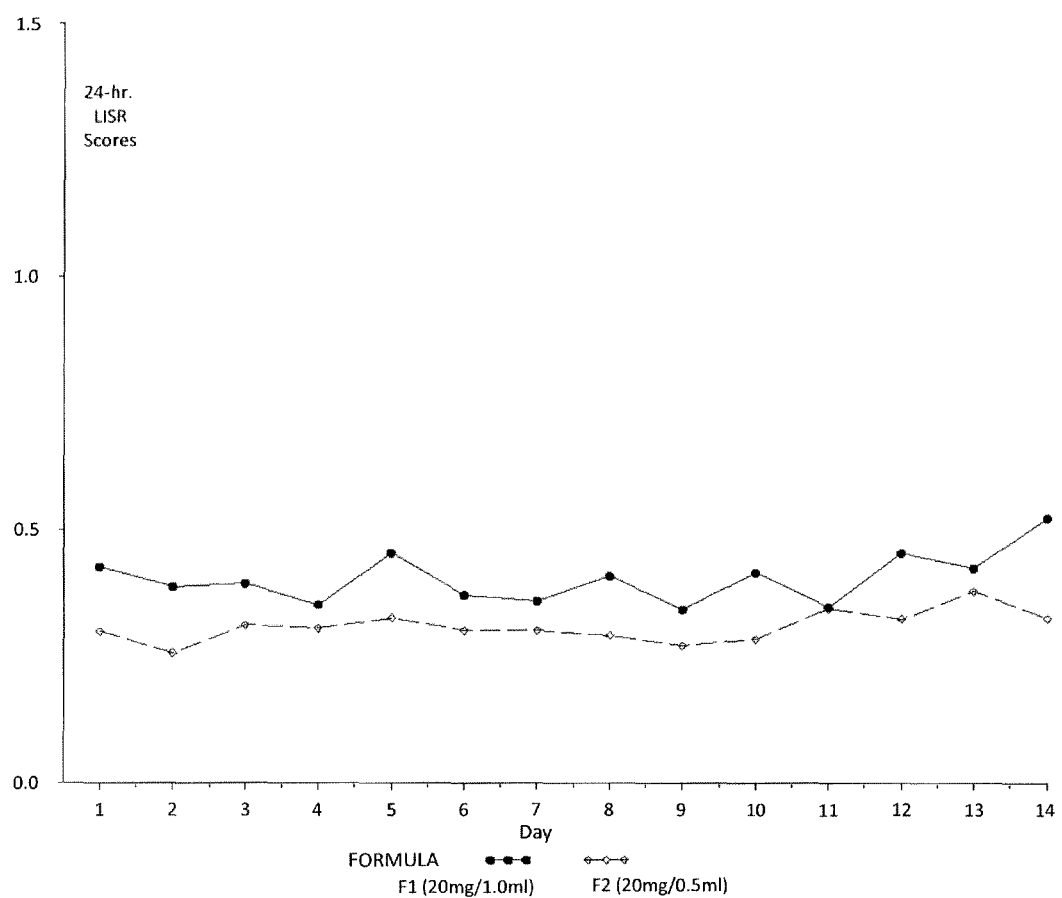
Figure 5C:
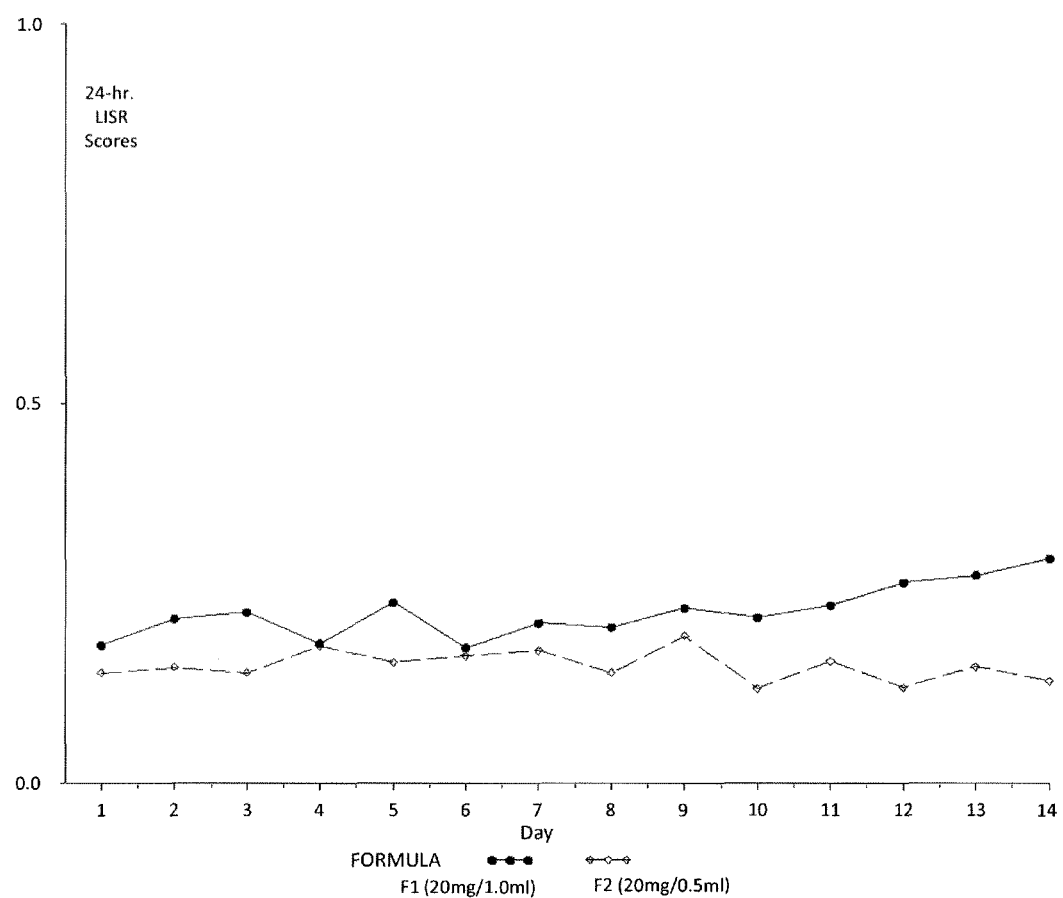
Figure 5D:
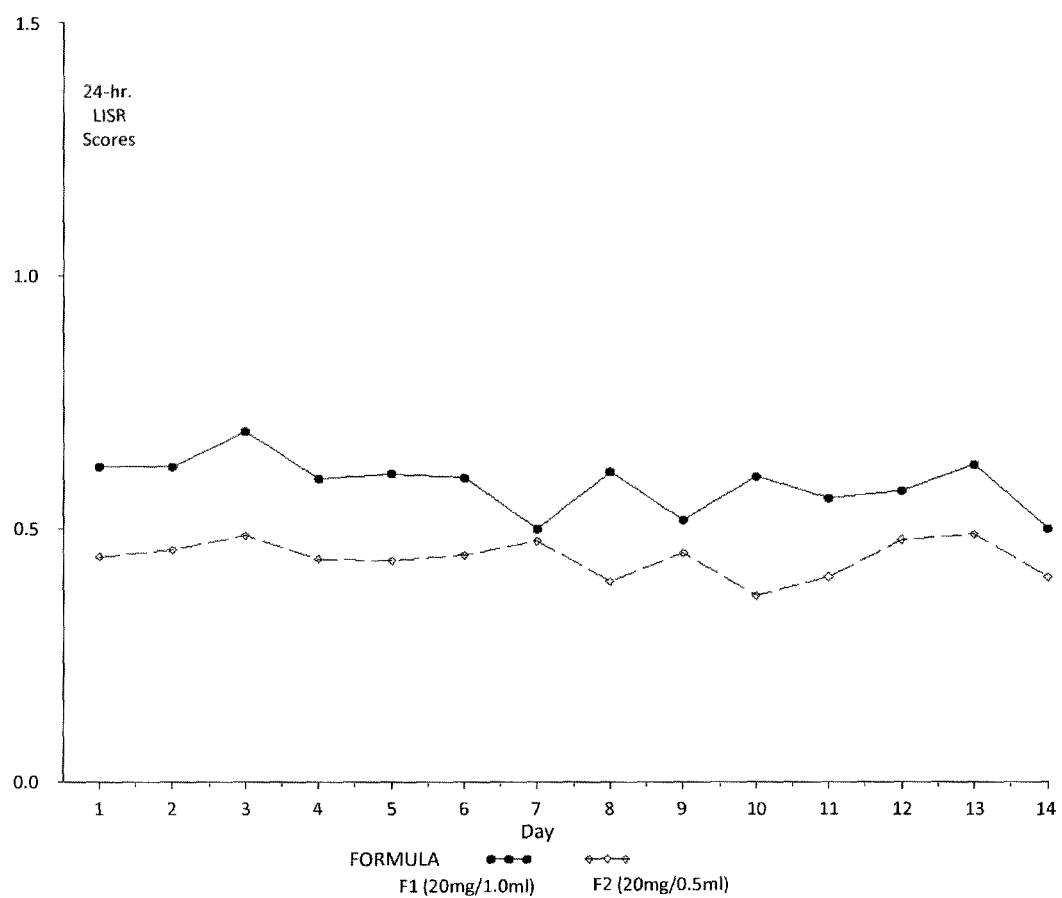

FIG. 3 presents the plot of daily total 5-minute VAS total scores for the ITT population.

Similar results were observed for the PP population with statistically significant difference (p<0.0001) in the 2 formulations of GA in favor of 20 mg/0.5 ml dose of GA.

TABLE 8

Analysis of Average 5-minute VAS Total Scores, ITT Population

| | | 20 mg/1.0 ml GA (N = 144) | 20 mg/0.5 ml GA (N = 144) | P-value [a] |
|---|---|---|---|---|
| VAS - 5-minute Scores | N | 143 | 144 | |
| | Mean | 17.19 | 11.85 | |
| | Standard Deviation | 18.583 | 14.112 | |
| | Median | 10.14 | 7.18 | |
| | Minimum, Maximum | (0.7, 84.4) | (0.6, 83.3) | |
| | Least Square Mean [a] | 157.6 | 130.4 | Period: 0.3104 |
| | 95% CI | (144.1, 171.2) | (116.9, 143.9) | Sequence: 0.7218 |
| | | | | Treatment: <0.0001 |
| | Comparison F1 to F2 [b] | | | |
| | Difference in LS Means [a] | 27.2 | | |
| | 95% CI for Difference | (20.2, 34.3) | | |
| | P-value | <.0001 | | |

CI = confidence interval;
F1 = 20 mg/1.0 ml formulation of GA:
F2 = 20 mg/0.5 ml formulation of GA;
GA = glatiramer acetate;
ITT = Intent-to-treat;
LS Means = least square means;
VAS = visual analogue scale.
[a] ANOVA model with mean ranked average 5-minute VAS score as the response; Sequence, Period, and Treatment as fixed effects and subject within sequence as random effect. Ranked data was used due to non-normality.
[b] Comparison of the 20 mg/1.0 ml GA drug formulation to the 20 mg/0.5 ml GA drug formulation.
Source: Table 14.2.2.2

Five-Minute LISR Presence Scores

Table 9 presents the analysis of average 5-minute LISR total presence scores for the ITT population. LISR total presence scores could range from 0 to 4 for an individual subject depending on how many of the following symptoms were experienced—redness, itching, swelling, and lump. The mean LISR total presence score was 1.85 at 5 minutes after administration of 20 mg/1.0 ml dose of GA and was 1.41 at 5 minutes after administration of 20 mg/0.5 ml dose of GA. In the comparison of the 2 treatments, the ranked VAS scores differed by 35.0 (95% CI: 25.4, 44.6) observations; this difference in the ranks was statistically significant (p<0.0001) in favor of 20 mg/0.5 ml dose of GA.

Similar results were observed in the PP population with statistically significant difference (p<0.0001) in the 2 formulations of GA in favor of 20 mg/0.5 ml dose of GA.

TABLE 9

Analysis of Average 5-minute LISR Total Presence Scores, ITT Population

| | | 20 mg/1.0 ml GA (N = 144) | 20 mg/0.5 ml GA (N = 144) | P-value [a] |
|---|---|---|---|---|
| 5-minute LISR Presence Scores | N | 143 | 144 | |
| | Mean | 1.85 | 1.41 | |
| | Standard Deviation | 0.988 | 0.991 | |
| | Median | 1.79 | 1.28 | |
| | Minimum, Maximum | (0.0, 4.0) | (0.0, 3.7) | |
| | Least Square Mean [a] | 161.3 | 126.2 | Period: 0.6382 |
| | 95% CI | (147.9, 174.7) | (112.9, 139.6) | Sequence: 0.5195 |
| | | | | Treatment: <0.0001 |
| | Comparison F1 to F2 [b] | | | |
| | Difference in LS Means [a] | 35.0 | | |
| | 95% CI for Difference | (25.4, 44.6) | | |
| | P-value | <.0001 | | |

CI = confidence interval;
F1 = 20 mg/1.0 ml formulation of GA;
F2 = 20 mg/0.5 ml formulation of GA;
GA = glatiramer acetate;
ITT = Intent-to-treat;
LS Means = least square means;
LISR = local injection site reaction
[a] ANOVA model with mean ranked average 5-minute LISR Presence score as the response; Sequence, Period, and Treatment as fixed effects and subject within sequence as random effect. Ranked data was used due to non-normality.
[b] Comparison of the 20 mg/1.0 ml GA drug formulation to the 20 mg/0.5 ml GA drug formulation.
Source: Table 14.2.5.1

Five-Minute LISR Severity Scores

Table 10 presents the analysis of average 5-minute LISR total severity scores for the ITT population. LISR total severity scores could range from 0 to 12 for an individual subject depending on the severity (rated 0 to 3) of each of the following symptoms experienced—redness, itching, swelling, and lump. The mean LISR total severity score was 2.30 at 5 minutes after administration of 20 mg/1.0 ml dose of GA and was 1.64 at 5 minutes after administration of 20 mg/0.5 ml dose of GA.

In the comparison of the 2 treatments, the ranked VAS scores differed by 36.9 (95% CI: 27.3, 46.5) observations; this difference in the ranks was statistically significant (p<0.0001) in favor of 20 mg/0.5 ml dose of GA.

Similar results were observed for the PP population with statistically significant difference (p<0.0001) in the 2 formulations of GA in favor of 20 mg/0.5 ml dose of GA.

TABLE 10

Analysis of Average 5-minute LISR Total Severity Scores, ITT Population

| | | 20 mg/1.0 ml GA (N = 144) | 20 mg/0.5 ml GA (N = 144) | P-value [a] |
|---|---|---|---|---|
| 5-minute LISR Scores | N | 143 | 144 | |
| | Mean | 2.30 | 1.64 | |
| | Standard Deviation | 1.549 | 1.361 | |
| | Median | 2.00 | 1.29 | |
| | Minimum, Maximum | (0.0, 7.6) | (0.0, 6.4) | |

TABLE 10-continued

Analysis of Average 5-minute LISR Total Severity Scores, ITT Population

|  | 20 mg/1.0 ml GA (N = 144) | 20 mg/0.5 ml GA (N = 144) | P-value [a] |
|---|---|---|---|
| Least Square Mean [a] | 162.2 | 125.3 | Period: 0.4573 |
| 95% CI | (148.9, 175.6) | (112.0, 138.6) | Sequence: 0.4351 |
|  |  |  | Treatment: <0.0001 |
| Comparison F1 to F2 [b] |  |  |  |
| Difference in LS Means [a] | 36.9 |  |  |
| 95% CI for Difference | (27.3, 46.5) |  |  |
| P-value | <.0001 |  |  |

CI = confidence interval;
F1 = 20 mg/1.0 ml formulation of GA;
F2 = 20 mg/0.5 ml formulation of GA;
GA = glatiramer acetate;
ITT = Intent-to-treat;
LS Means = least square means;
LISR = local injection site reaction
[a] ANOVA model with mean ranked average 5-minute LISR score as the response; Sequence, Period, and Treatment as fixed effects and subject within sequence as random effect. Ranked data was used due to non-normality.
[b] Comparison of the 20 mg/1.0 ml GA drug formulation to the 20 mg/0.5 ml GA drug formulation.

Twenty-Four Hour LISR Presence Scores

Table 11 presents the analysis of average 24-hour LISR total presence scores for the ITT population. The mean LISR total presence score was 1.19 at 24 hours after administration of 20 mg/1.0 ml dose of GA and was 0.92 at 24 hours after administration of 20 mg/0.5 ml dose of GA. In the comparison of the 2 treatments, the ranked VAS scores differed by 23.8 (95% CI: 14.9, 32.6) observations; this difference in the ranks was statistically significant (p<0.0001) in favor of 20 mg/0.5 ml dose of GA.

TABLE 11

Analysis of Average 24-hour LISR Total Presence Scores, ITT Population

|  |  | 20 mg/1.0 ml GA (N = 144) | 20 mg/0.5 ml GA (N = 144) | P-value [a] |
|---|---|---|---|---|
| 24-hour | N | 143 | 144 |  |
| LISR | Mean | 1.19 | 0.92 |  |
| Presence | Standard Deviation | 0.981 | 0.894 |  |
| Scores | Median | 1.00 | 0.69 |  |
|  | Minimum, Maximum | (0.0, 4.0) | (0.0, 3.9) |  |
|  | Least Square Mean [a] | 155.8 | 132.0 | Period: 0.9731 |
|  | 95% CI | (142.2, 169.3) | (118.5, 145.6) | Sequence: 0.8711 |
|  |  |  |  | Treatment: <0.0001 |
|  | Comparison F1 to F2 [b] |  |  |  |
|  | Difference in LS Means [a] | 23.8 |  |  |
|  | 95% CI for Difference | (14.9, 32.6) |  |  |
|  | P-value | <.0001 |  |  |

CI = confidence interval;
F1 = 20 ml/1.0 ml formulation of GA;
F2 = 20 mg/0.5 ml formulation of GA;
GA = glatiramer acetate;
ITT = Intent-to-treat;
LS Means = least square means;
LISR = local injection site reaction
[a] ANOVA model with mean ranked average 24-hour LISR Presence score as the response; Sequence, Period, and Treatment as fixed effects and subject within sequence as random effect. Ranked data was used due to non-normality.
[b] Comparison of the 20 mg/1.0 ml GA drug formulation to the 20 mg/0.5 ml GA drug formulation.

Similar results were observed in the PP population with statistically significant difference (p<0.0001) in the 2 formulations of GA in favor of 20 mg/0.5 ml dose of GA.

Twenty-Four Hour LISR Total Severity Scores

Table 12 presents the analysis of average 24-hour LISR total severity scores for the ITT population. The mean LISR total severity score was 1.47 at 24 hours after administration of 20 mg/1.0 ml dose of GA and was 1.10 at 24 hours after administration of 20 mg/0.5 ml dose of GA.

In the comparison of the 2 treatments, the ranked VAS scores differed by 23.8 (95% CI: 15.0, 32.7) observations; this difference in the ranks was statistically significant (p<0.0001) in favor of 20 mg/0.5 ml dose of GA.

TABLE 12

Analysis of Average 24-hour LISR Total Severity Scores, ITT Population

| | | 20 mg/1.0 ml GA (N = 144) | 20 mg/0.5 ml GA (N = 144) | P-value [a] |
|---|---|---|---|---|
| 24-hour LISR Scores | N | 143 | 144 | |
| | Mean | 1.47 | 1.10 | |
| | Standard Deviation | 1.370 | 1.225 | |
| | Median | 1.00 | 0.69 | |
| | Minimum, Maximum | (0.0, 6.5) | (0.0, 7.7) | |
| | Least Square Mean [a] | 155.8 | 132.0 | Period: 0.6346 |
| | 95% CI | (142.2, 169.4) | (118.4, 145.5) | Sequence: 0.9096 |
| | | | | Treatment: <0.0001 |
| | Comparison F1 to F2 [b] | | | |
| | Difference in LS Means [a] | 23.8 | | |
| | 95% CI for Difference | (15.0, 32.7) | | |
| | P-value | <.0001 | | |

CI = confidence interval;
F1 = 20 mg/1.0 ml formulation or GA;
F2 = 20 mg/0.5 ml formulation of GA;
GA = glatiramer acetate;
ITT = Intent-to-treat;
LS Means = least square means;
LISR = local injection site reaction
[a] ANOVA model with mean ranked average 24-hour LISR score as the response; sequence, period, and treatment as fixed effects and subject within sequence as random effect. Ranked data was used due to non-normality.
[b] Comparison of the 20 mg/1.0 ml GA drug formulation to the 20 mg/0.5 ml GA drug formulation.

Similar results were observed in the PP population with statistically significant difference (p<0.0001) in the 2 formulations of GA in favor of 20 mg/0.5 ml dose of GA.

Additional Observations

Injections of F2 are at least as effective as injections of F1 in treating RRMS.

Exploratory Clinical Measurements

Average Immediate VAS Pain Presence Total Scores

Table 13 below presents the analysis of average immediate pain presence total scores for the ITT population (Pain scores were dichotomized as either No Pain=0 (a VAS score of 0-4 mm), or Pain=1 (a VAS score of 5-100 mm; see page 55-56 "Exploratory Outcome Measures"). The mean immediate VAS pain presence total score was 0.53 after administration of 20 mg/1.0 ml dose of GA and was 0.43 after administration of 20 mg/0.5 ml dose of GA. This suggests that the pain following injection of 20 mg/1.0 ml dose of GA was greater than the pain following injection of 20 mg/0.5 ml dose of GA.

In the comparison of the 2 treatments, the ranked VAS pain presence scores differed by 20.3 (95% CI: 12.0, 28.6) observations; this difference in the ranks was statistically significant (p<0.0001) in favor of 20 mg/0.5 ml dose of GA.

TABLE 13

Analysis of Average Immediate VAS Pain Presence Total Scores, ITT Population

| | | 20 mg/1.0 ml GA (N = 144) | 20 mg/0.5 ml GA (N = 144) | P-value [a] |
|---|---|---|---|---|
| Immediate Pain Presence Scores | N | 143 | 144 | |
| | Mean | 0.53 | 0.43 | |
| | Standard Deviation | 0.394 | 0.391 | |
| | Median | 0.47 | 0.30 | |
| | Minimum, Maximum | (0.0, 1.0) | (0.0, 1.0) | |
| | Least Square Mean [a] | 154.1 | 133.8 | Period: 0.7788 |
| | 95% CI | (140.6, 167.6) | (120.3, 147.3) | Sequence: 0.6358 |
| | | | | Treatment: <.0001 |
| | Comparison F1 to F2 [b] | | | |
| | Difference in LS Means [a] | 20.3 | | |
| | 95% CI for Difference | (12.0, 28.6) | | |
| | P-value | <.0001 | | |

CI = confidence interval;
F1 = 20 mg/1.0 ml formulation of GA;
F2 = 20 mg/0.5 ml formulation of GA;
GA = glatiramer acetate;
ITT = Intent-to-treat;
LS Means = least square means

[a] ANOVA model with mean ranked average Pain Presence score as the response; sequence, period, and treatment as fixed effects and subject within sequence as random effect. Ranked data was used due to non-normality.
[b] Comparison of the 20 mg/1.0 ml GA drug formulation to the 20 mg/0.5 ml GA drug formulation.

Average 5-Minute VAS Pain Presence Total Scores

Table 14 presents the analysis of average 5-minute VAS pain presence total scores for the ITT population (Pain scores were dichotomized as either No Pain=0 (a VAS score of 0-4 mm), or Pain=1 (a VAS score of 5-100 mm; see page 55-56 "Exploratory Outcome Measures"). The mean VAS pain presence total score was 0.67 at 5 minutes after administration of 20 mg/1.0 ml dose of GA and was 0.54 at 5 minutes after administration of 20 mg/0.5 ml dose of GA. In the comparison of the 2 treatments, the ranked 5-minute VAS pain presence total scores differed by 27.0 (95% CI: 19.0, 34.9) observations; this difference in the ranks was statistically significant (p<0.0001) in favor of 20 mg/0.5 ml dose of GA.

TABLE 14

Analysis of Average 5-minute Pain Presence Total Scores, ITT Population

| | | 20 mg/1.0 ml GA (N = 144) | 20 mg/0.5 ml GA (N = 144) | P-value [a] |
|---|---|---|---|---|
| 5-minute Pain Presence Scores | N | 143 | 144 | |
| | Mean | 0.67 | 0.54 | |
| | Standard Deviation | 0.375 | 0.394 | |
| | Median | 0.87 | 0.55 | |
| | Minimum, Maximum | (0.0, 1.0) | (0.0, 1.0) | |
| | Least Square Mean [a] | 157.3 | 130.3 | Period: 0.9127 |
| | 95% CI | (144.1, 170.5) | (117.1, 143.5) | Sequence: 0.3600 |
| | | | | Treatment: <0.0001 |
| | Comparison F1 to F2 [b] | | | |
| | Difference in LS Means [a] | 27.0 | | |
| | 95% CI for Difference | (19.0, 34.9) | | |
| | P-value | <.0001 | | |

CI = confidence interval;
F1 = 20 mg/1.0 ml formulation of GA;
F2 = 20 mg/0.5 ml formulation of GA;
GA = glatiramer acetate;
ITT = Intent-to-treat;
LS Means = least square means
[a] ANOVA model with mean ranked average 5-minute Pain Presence score as the response; sequence, period, and treatment as fixed effects and subject within sequence as random effect. Ranked data was used due to non-normality.
[b] Comparison of the 20 mg/1.0 ml GA drug formulation to the 20 mg/0.5 ml GA drug formulation.

Average Daily 5-Minute LISR Scores

Table 15 presents the average daily 5-minute LISR scores for the ITT population. Plot of average daily 5-minute LISR scores is presented for the ITT population in FIG. 4(A-D). Swelling, redness, itching and lump were the 4 symptoms considered as local injection site reactions during the study. The mean LISR scores for each of these symptoms were lower for subjects receiving 20 mg/0.5 ml dose of GA than for subjects receiving 20 mg/1.0 ml dose of GA at 5 minutes after administration of injections at each visit.

TABLE 15

Average Daily 5-minute LISR Scores, ITT Population

| LISR Symptom | | 20 mg/1.0 ml GA (N = 144) | 20 mg/0.5 ml GA (N = 144) |
|---|---|---|---|
| Swelling | | | |
| Day 1 | N | 143 | 144 |
| | Mean (SD) | 0.47 (0.739) | 0.34 (0.605) |
| | Median | 0.00 | 0.00 |
| | Minimum, Maximum | (0.0, 3.0) | (0.0, 2.0) |
| Day 14 | N | 140 | 133 |
| | Mean (SD) | 0.42 (0.669) | 0.25 (0.499) |
| | Median | 0.00 | 0.00 |
| | Minimum, Maximum | (0.0, 3.0) | (0.0, 2.0) |
| Redness | | | |
| Day 1 | N | 143 | 144 |
| | Mean (SD) | 0.70 (0.702) | 0.62 (0.719) |
| | Median | 1.00 | 0.50 |
| | Minimum, Maximum | (0.0, 3.0) | (0.0, 3.0) |
| Day 14 | N | 140 | 134 |
| | Mean (SD) | 0.74 (0.653) | 0.50 (0.572) |
| | Median | 1.00 | 0.00 |
| | Minimum, Maximum | (0.0, 3.0) | (0.0, 2.0) |
| Itching | | | |
| Day 1 | N | 142 | 144 |
| | Mean (SD) | 0.45 (0.669) | 0.31 (0.585) |
| | Median | 0.00 | 0.00 |
| | Minimum, Maximum | (0.0, 3.0) | (0.0, 2.0) |
| Day 14 | N | 140 | 133 |
| | Mean (SD) | 0.46 (0.650) | 0.26 (0.475) |
| | Median | 0.00 | 0.00 |
| | Minimum, Maximum | (0.0, 2.0) | (0.0, 2.0) |
| Lump | | | |
| Day 1 | N | 142 | 144 |
| | Mean (SD) | 0.64 (0.656) | 0.47 (0.636) |
| | Median | 1.00 | 0.00 |
| | Minimum, Maximum | (0.0, 3.0) | (0.0, 3.0) |

TABLE 15-continued

Average Daily 5-minute LISR Scores, ITT Population

| LISR Symptom | | 20 mg/1.0 ml GA (N = 144) | 20 mg/0.5 ml GA (N = 144) |
|---|---|---|---|
| Day 14 | N | 140 | 133 |
| | Mean (SD) | 0.68 (0.712) | 0.47 (0.558) |
| | Median | 1.00 | 0.00 |
| | Minimum, Maximum | (0.0, 3.0) | (0.0, 2.0) |

GA = glatiramer acetate;
ITT = Intent-to-treat;
SD = Standard deviation

Average Daily 24-Hour LISR Scores

Table 16 presents the average daily 24-hour LISR scores for the ITT population. The plot of average daily 24-hour LISR scores is presented for the ITT population in FIG. 5(A-D). The mean LISR scores for each of these symptoms were lower for subjects receiving 20 mg/0.5 ml dose of GA than for subjects receiving 20 mg/1.0 ml dose of GA at 24 hours after administration of injections at each visit.

TABLE 16

Average Daily 24-hour LISR Scores, ITT Population

| LISR Symptom | | 20 mg/1.0 ml GA (N = 144) | 20 mg/0.5 ml GA (N = 144) |
|---|---|---|---|
| Swelling | | | |
| Day 1 | N | 143 | 144 |
| | Mean (SD) | 0.29 (0.539) | 0.20 (0.467) |
| | Median | 0.00 | 0.00 |
| | Minimum, Maximum | (0.0, 3.0) | (0.0, 2.0) |
| Day 14 | N | 44 | 37 |
| | Mean (SD) | 0.39 (0.655) | 0.16 (0.442) |
| | Median | 0.00 | 0.00 |
| | Minimum, Maximum | (0.0, 2.0) | (0.0, 2.0) |
| Redness | | | |
| Day 1 | N | 143 | 144 |
| | Mean (SD) | 0.43 (0.587) | 0.30 (0.503) |
| | Median | 0.00 | 0.00 |
| | Minimum, Maximum | (0.0, 2.0) | (0.0, 2.0) |
| Day 14 | N | 44 | 37 |
| | Mean (SD) | 0.52 (0.664) | 0.32 (0.580) |
| | Median | 0.00 | 0.00 |
| | Minimum, Maximum | (0.0, 2.0) | (0.0, 2.0) |
| Itching | | | |
| Day 1 | N | 143 | 144 |
| | Mean (SD) | 0.18 (0.405) | 0.15 (0.442) |
| | Median | 0.00 | 0.00 |
| | Minimum, Maximum | (0.0, 2.0) | (0.0, 2.0) |
| Day 14 | N | 44 | 37 |
| | Mean (SD) | 0.30 (0.553) | 0.14 (0.419) |
| | Median | 0.00 | 0.00 |
| | Minimum, Maximum | (0.0, 2.0) | (0.0, 2.0) |
| Lump | | | |
| Day 1 | N | 143 | 144 |
| | Mean (SD) | 0.62 (0.700) | 0.44 (0.623) |
| | Median | 1.00 | 0.00 |
| | Minimum, Maximum | (0.0, 3.0) | (0.0, 3.0) |
| Day 14 | N | 44 | 37 |
| | Mean (SD) | 0.50 (0.731) | 0.41 (0.644) |
| | Median | 0.00 | 0.00 |
| | Minimum, Maximum | (0.0, 3.0) | (0.0, 2.0) |

GA = glatiramer acetate;
ITT = Intent-to-treat;
SD = Standard deviation

No Symptoms at 5 Minutes Post-injection

Table 17 presents the number and percent of subjects reporting no symptoms at 5 minutes following injection for the ITT population. Most subjects reported some symptoms 5 minutes following injection of either formulation. However, the number and percentage of subjects reporting no symptoms at 5 minutes after 20 mg/0.5 ml GA injection was two to three times the number and percentage of subjects reporting no symptoms at 5 minutes after 20 mg/1.0 ml GA injection for each day interval.

TABLE 17

Number and Percent of Subjects Reporting No Symptoms 5-minutes Following Injection, ITT Population

| | Day Intervals | 20 mg/1.0 ml GA (N = 144) | 20 mg/0.5 ml GA (N = 144) |
|---|---|---|---|
| LISR Symptoms | 0-3 | 6 (4.2%) | 16 (11.1%) |
| | 4-6 | 10 (6.9%) | 19 (13.2%) |
| | 7-9 | 12 (8.3%) | 23 (16.0%) |
| | >9 | 6 (4.2%) | 20 (13.9%) |

GA = glatiramer acetate;
ITT = Intent-to-treat

No Symptoms at 24 Hours Post-Injection

Table 18 presents the number and percent of subjects reporting no symptoms 24 hours following injection for the ITT population. The majority of subjects reported symptoms 24 hours following injection of either formulation; however there were fewer subjects reporting symptoms 24 hours following injection than those reporting at 5 minutes following injections. The number and percentage of subjects reporting no symptoms after 24 hours following injection of 20 mg/0.5 ml GA was approximately 25%-50% higher than the number and percentage of subjects reporting no symptoms after 24 hours following injection of 20 mg/1.0 ml GA for most day intervals.

TABLE 18

Number and Percent of Subjects Reporting No Symptoms 24-hours Following Injection, ITT Population

| | Day Intervals | 20 mg/1.0 ml GA (N = 144) | 20 mg/0.5 ml GA (N = 144) |
|---|---|---|---|
| LISR Symptoms | 0-3 | 28 (19.4%) | 36 (25.0%) |
| | 4-6 | 29 (20.1%) | 43 (29.9%) |
| | 7-9 | 35 (24.3%) | 47 (32.6%) |
| | >9 | 7 (4.9%) | 16 (11.1%) |

GA = glatiramer acetate;
ITT = Intent-to-treat

Symptoms at 5 Minutes Following Injection by Injection Site

Table 19 presents the number and percent of subjects reporting symptoms at 5-minutes following injection by injection site for the ITT population. Overall, the number and percentage of subjects reporting symptoms at 5 minutes following injection of 20 mg/0.5 ml GA was less than the number and percentage of subjects reporting symptoms at 5 minutes following injection of 20 mg/1.0 ml GA with the exception of redness in the left arm and itching in the right arm.

TABLE 19

Number and Percent of Subjects Reporting Symptoms 5-Minutes Following Injection by Injection Site, ITT Population

| Injection site | Symptoms | 20 mg/1.0 ml GA (N = 144) | 20 mg/0.5 ml GA (N = 144) |
|---|---|---|---|
| Stomach | | n = 138 | n = 138 |
| | Swelling | 59 (42.8) | 43 (31.2) |
| | Redness | 108 (78.3) | 88 (63.8) |
| | Itching | 70 (50.7) | 60 (43.5) |
| | Lump | 83 (60.1) | 70 (50.7) |
| Left Arm | | n = 111 | n = 113 |
| | Swelling | 60 (54.1) | 44 (38.9) |
| | Redness | 73 (65.8) | 75 (66.4) |
| | Itching | 49 (44.1) | 42 (37.2) |
| | Lump | 79 (71.2) | 67 (59.3) |
| Right Arm | | n = 111 | n = 111 |
| | Swelling | 50 (45.0) | 41 (36.9) |
| | Redness | 78 (70.3) | 64 (57.7) |
| | Itching | 41 (36.9) | 46 (41.4) |
| | Lump | 86 (77.5) | 63 (56.8) |
| Left Thigh | | n = 136 | n = 139 |
| | Swelling | 69 (50.7) | 64 (46.0) |
| | Redness | 98 (72.1) | 94 (67.6) |
| | Itching | 70 (51.5) | 45 (32.4) |
| | Lump | 102 (75.0) | 76 (54.7) |
| Right Thigh | | n = 139 | n = 139 |
| | Swelling | 69 (49.6) | 61 (43.9) |
| | Redness | 107 (77.0) | 93 (66.9) |
| | Itching | 66 (47.5) | 48 (34.5) |
| | Lump | 95 (68.3) | 89 (64.0) |
| Left Hip | | n = 140 | n = 141 |
| | Swelling | 54 (38.6) | 47 (33.3) |
| | Redness | 98 (70.0) | 83 (58.9) |
| | Itching | 62 (44.3) | 52 (36.9) |
| | Lump | 84 (60.0) | 66 (46.8) |
| Right Hip | | n = 140 | n = 141 |
| | Swelling | 49 (35.0) | 42 (29.8) |
| | Redness | 97 (69.3) | 80 (56.7) |
| | Itching | 63 (45.0) | 51 (36.2) |
| | Lump | 87 (62.1) | 67 (47.5) |

GA = glatiramer acetate;
ITT = Intent-to-treat
Note:
Included subjects reporting at least once within a period. Each subject was counted once within symptom, however, they could have been counted for each symptom experienced within a site.

Symptoms at 24 Hours Following Injection by Injection Site

Table 20 presents the number and percent of subjects reporting symptoms at 24-hours following injection by injection site for the ITT population. Overall, the number and percentage of subjects reporting symptoms at 24 hours following injection of 20 mg/0.5 ml GA was less than the number and percentage of subjects reporting symptoms at 24 hours following injection of 20 mg/1.0 ml GA with the exception of redness when the left arm was the injection site.

TABLE 20

Number and Percent of Subjects Reporting Symptoms 24-hours Following Injection by Injection Site, ITT Population

| Injection site | Symptoms | 20 mg/1.0 ml GA (N = 144) | 20 mg/0.5 ml GA (N = 144) |
|---|---|---|---|
| Stomach | | n = 138 | n = 137 |
| | Swelling | 38 (27.5) | 35 (25.5) |
| | Redness | 73 (52.9) | 60 (43.8) |
| | Itching | 40 (29.0) | 30 (21.9) |
| | Lump | 67 (48.6) | 64 (46.7) |
| Left Arm | | n = 110 | n = 113 |
| | Swelling | 36 (32.7) | 32 (28.3) |
| | Redness | 41 (37.3) | 45 (39.8) |
| | Itching | 33 (30.0) | 24 (21.2) |
| | Lump | 66 (60.0) | 62 (54.9) |
| Right Arm | | n = 111 | n = 111 |
| | Swelling | 33 (29.7) | 24 (21.6) |
| | Redness | 43 (38.7) | 35 (31.5) |
| | Itching | 33 (29.7) | 27 (24.3) |
| | Lump | 68 (61.3) | 56 (50.5) |
| Left Thigh | | n = 136 | n = 139 |
| | Swelling | 51 (37.5) | 31 (22.3) |
| | Redness | 66 (48.5) | 54 (38.8) |
| | Itching | 36 (26.5) | 22 (15.8) |
| | Lump | 83 (61.0) | 66 (47.5) |
| Right Thigh | | n = 139 | n = 139 |
| | Swelling | 55 (39.6) | 41 (29.5) |
| | Redness | 63 (45.3) | 57 (41.0) |
| | Itching | 36 (25.9) | 22 (15.8) |
| | Lump | 84 (60.4) | 77 (55.4) |
| Left Hip | | n = 139 | n = 141 |
| | Swelling | 28 (20.1) | 27 (19.1) |
| | Redness | 51 (36.7) | 40 (28.4) |
| | Itching | 31 (22.3) | 31 (22.0) |
| | Lump | 75 (54.0) | 59 (41.8) |
| Right Hip | | n = 138 | n = 141 |
| | Swelling | 29 (21.0) | 20 (14.2) |
| | Redness | 60 (43.5) | 42 (29.8) |
| | Itching | 33 (23.9) | 26 (18.4) |
| | Lump | 79 (57.2) | 62 (44.0) |

GA = glatiramer acetate;
ITT = Intent-to-treat
Note:
Included subjects reporting at least once within a period. Each subject was counted once within symptom, however, they could have been counted for each symptom experienced within a site.

Comparison of 20 mg/0.5 ml Unit Dosage Form to 40 mg/ml Unit Dosage Form

The 20 mg/0.5 ml formulation exhibits surprising properties in clinical testing in view of the 20 mg/ml and 40 mg/ml formulations.

As indicated in Table 21 hereinbelow, the 40 mg/ml solution of glatiramer acetate is no more effective than administering a 20 mg/ml dose (42). The doubling of the drug dosage together with a doubling of drug concentration did not lead to a doubling in the efficacy to the patient (40-42). Thus, doubling both the amount of active drug and the drug concentration does not double the efficacy of the unit dosage form. In fact, the prior art indicates that doubling drug concentration may have inhibited the effectiveness of the drug.

TABLE 21

Comparison of glatiramer acetate formulations

| | 20 mg/1 ml(39) | 40 mg/1 ml(40-42) | 20 mg/0.5 ml |
|---|---|---|---|
| Content | 20 mg glatiramer acetate | 40 mg glatiramer acetate | 20 mg glatiramer acetate |
| | 40 mg mannitol | 40 mg mannitol | 20 mg mannitol |
| | 1 ml water for injection | 1 ml water for injection | 0.5 ml water for injection |

TABLE 21-continued

Comparison of glatiramer acetate formulations

| | 20 mg/1 ml(39) | 40 mg/1 ml(40-42) | 20 mg/0.5 ml |
|---|---|---|---|
| Effectivity | Reduction in GD-enhancing lesions | Same(42) | Same (see pg. 24, lines 13-15 and pg. 80, lines 4-5) |
| | Reduction in Mean Relapse rate | Same(42) | Same (see pg. 19, lines 3-9 and pg. 80, lines 4-5) |
| Adverse reactions | | | |
| Occurrence of Immediate Post-Injection reactions (IPIRs) | 22.7% of subjects | 32.6% of subjects (43.6% increase over 20 mg/ml)[40] | |
| IPIRs (flushing, chest pain, palpitations, Anxiety, dyspna, throat constriction, urticaria) | Mild severity | Moderate severity(40) | |
| Injection site reactions | burning, mass, pain, and urticartia are observed | 5% higher incidence of reactions relative to 20 mg/ml(40) | |
| patient-reported total injection pain rating on a visual analogue scale (VAS) occurring immediately after injection | VAS scores taken as baseline | | Reduced by about 27% relative to those present for 20 mg/ml (see page 15, lines 26-27 of the subject application) |
| the patient-reported total injection pain rating on a visual analogue scale (VAS) experienced five minutes following the subcutaneous injection | VAS scores taken as baseline | | Reduced by about 31% relative to those present for 20 mg/ml (see page 16, lines 5-7 of the subject application) |
| Immediate pain presence | Dichotomized VAS scores taken as baseline | | Reduced by about 19% relative to those present for 20 mg/ml (see page 16, lines 10-11 of the subject application) |
| Pain presence five minutes following the subcutaneous injection | Dichotomized VAS scores taken as baseline | | Reduced by about 19% relative to those present for 20 mg/ml (see page 16, lines 14-16 of the subject application) |
| Number of Local Injection Site Reactions (LISRs) five minutes after the subcutaneous injection | Number taken as baseline | | Reduced by about 24% relative to those present for 20 mg/ml (see page 17, lines 1-3 of the subject application) |
| Severity of Local Injection Site Reactions (LISRs) five minutes after the subcutaneous injection | | | Reduced by about 29% relative to those present for 20 mg/ml (see page 17, lines 4-6 of the subject application) |

TABLE 21-continued

Comparison of glatiramer acetate formulations

| | 20 mg/1 ml(39) | 40 mg/1 ml(40-42) | 20 mg/0.5 ml |
|---|---|---|---|
| Number of Local Injection Site Reactions (LISRs) 24 hours after the subcutaneous injection | Number taken as baseline | | Reduced by about 23% relative to those present for 20 mg/ml (see page 17, lines 10-12 of the subject application) |
| Severity of Local Injection Site Reactions (LISRs) 24 hours after the subcutaneous injection | Scores taken as baseline | | Reduced by about 25% relative to those present for 20 mg/ml (see page 17, lines 13-15 of the subject application) |
| Daily five-minute Local Injection Site Reaction (LISR) score: swelling, redness, itching, lump | Score taken as baseline | | Reduced relative to those present for 20 mg/ml (see page 17, lines 16-21 of the subject application) |
| Daily 24-hour Local Injection Site Reaction (LISR) score: swelling, redness, itching, lump | Score taken as baseline | | reduced relative to those present for 20 mg/ml (see page 17, lines 22-26 of the subject application) |

In summary, the 20 mg/0.5 ml form of glatiramer acetate represents a unique and novel formulation that differs from prior art formulations of glatiramer acetate. Specifically:

1) Physically, 20 mg/0.5 ml, is delivered in half the volume disclosed in the prior art (1 ml) and comprises half the amount of mannitol i.e., 20 mg.
2) Despite these physical differences, the 20 mg/0.5 ml formulation is at least as effective as either the prior art formulations of 20 mg/1 ml or 40 mg/ml glatiramer acetate (see Table 21 above).
3) Applicants' clinical trial data revealed that the 40 mg/ml glatiramer acetate formulation is associated with a significant increase in adverse reactions i.e., occurrence of immediate post-injection reactions (IPIRs), severity of IPIRs, and incidence of injection site reactions (see Table 21 above).
4) In contrast, applicants have discovered through clinical trial that the new formulation of 20 mg/0.5 ml induces less pain and both fewer and less severe injection site reactions (see Table 21 above).

Discussion

Rapid advancements in biotechnology have led to the development of many peptide therapeutics. Successful clinical use of such peptide therapeutics requires proper formulation. The most conventional route of delivery for protein drugs that require frequent and chronic administration is subcutaneous injection (25). When combined with prefilled syringe and autoinjector device technology, subcutaneous delivery allows for home administration and improved compliance of administration. However, despite the advantages of subcutaneous injection there exist several obstacles and limitations associated with subcutaneous drug delivery. Firstly, limits on the acceptable injection volume pose a major disadvantage. Typically no more than 1 to 2 ml of solution is permitted (26). Secondly, the potential exists for drug degradation at the site of injection resulting in reduced bioavailability. Thirdly, based on the physiochemical properties of the drug, potent compounds may become locally trapped in the interstitial space which can lead to further localized irritation, precipitation of the drug and concentration-dependent adverse effects (26).

Thus, despite the advancements in biological therapeutics, there still exists a need for improved methods of subcutaneous drug delivery. In particular there is a need for reliable concentrated drug preparations, allowing for reduced injection volumes while preserving drug activity and stability.

Clinical Outcomes

This was a multicenter, randomized, two-arm, single crossover study to compare the tolerability and safety of 2 formulations of GA: 20 mg/1.0 ml (F1) versus 20 mg/0.5 ml (F2) administered subcutaneously in subjects with RRMS. Subjects were to receive both doses once daily in a crossover fashion, for a total treatment duration of 5 weeks.

The primary clinical outcome variable was the total injection pain rating occurring immediately after injection (i.e., immediate total pain score). Pain immediately following injection and at later timepoints was relatively low for both formulations. However, the mean immediate VAS total pain score was less after administration of 20 mg/0.5 ml GA injection compared with 20 mg/1.0 ml GA injection. The difference in ranked scores between the 2 formulations of GA was statistically significant ($p<0.0001$) in favor of 20 mg/0.5 ml dose.

Pain occurring immediately after injection and at five minutes was lower with 20 mg/0.5 ml formulation of GA compared with 20 mg/1.0 ml formulation of GA; the difference in the ranked scores was statistically significant ($p<0.0001$). The secondary clinical outcomes were daily VAS pain scores (at 5 minutes post-injection), and the incidence and severity of LIRSs (at 5 minutes and 24 hours post-injection), by study drug formulation. The total VAS pain score at 5 minutes post-dose was less for 20 mg/0.5 ml injection of GA compared with 20 mg/1.0 ml injection of GA.

Similarly the subject-reported incidence and severity of LISRs were lower with 20 mg/0.5 ml GA injection compared with 20 mg/1.0 ml GA injection at five minutes and 24 hours post-dose; the difference in the ranked scores was statistically significant (p<0.0001).

Exploratory analyses supported the finding of the primary and secondary analyses. The mean pain presence scores were lower immediately and at five minutes post injection with 20 mg/0.5 ml dose of GA compared with 20 mg/1.0 ml dose of GA. A greater number and percentage of subjects reported no symptoms after five minutes and after 24 hours of injection of 20 mg/0.5 ml GA versus after receiving an injection of 20 mg/1.0 ml GA. The LISRs data were further considered by splitting the subjects according to the presence or absence of symptoms. Only 4% to 16% of subjects reported no symptoms at five minutes following injection across both formulations during Day 0-3, Day 4-6, Day 7-9 and following Day 9; however, the rate of subjects with no symptoms was approximately two to three times higher following the 20 mg/0.5 ml formulation than the 20 mg/1.0 ml formulation. By 24 hours post-injection, 4% to 33% of subjects reported no symptoms across both formulations during Day 0-3, Day 4-6, Day 7-9 and following Day 9; the rate following 20 mg/0.5 ml was 50% higher than that following the other formulation.

Safety Conclusions

A greater number and percentage of subjects reported no symptoms after five minutes and after 24 hours of injection of 20 mg/0.5 ml GA versus after receiving an injection of 20 mg/1.0 ml GA. The percentage of subjects reporting TEAEs was low (<20%) for both treatments. A total of 27 TEAEs were reported for 18 (12.5%) subjects following 20 mg/1.0 ml GA injection and 38 TEAEs were reported for 26 (18.1%) subjects following 20 mg/0.5 ml GA injection. The most frequently reported TEAEs after administration of 20 mg/0.5 ml GA injection were urinary tract infection (2.8%), and viral upper respiratory tract infection, arthralgia, and headache (1.4% each). The most frequently reported TEAEs after administration of 20 mg/1.0 ml GA injection were contusion, muscular weakness, and ataxia (1.4% each). Overall, 2 severe TEAEs were reported during the study: severe biliary dyskinesia during the run-in period and severe hypertonia after administration of 20 mg/1.0 ml GA injection. Both events were not related to the study treatment and resolved in a day or two. All other TEAEs were either mild or moderate in intensity.

Overall, 3 (2.1%) subjects following 20 mg/1.0 ml GA injection and (2.8%) subjects following 20 mg/0.5 ml GA injection had treatment-related TEAEs. The treatment-related TEAEs were constipation, injection site nodule, headache, panic attack, and dyspnoea reported for 1 (0.7%) subject each after administration of 20 mg/0.5 ml GA injection; and hepatic enzyme increased, headache, anxiety and panic attack reported for 1 (0.7%) subject each after administration of 20 mg/1.0 ml GA injection.

The mean changes from baseline in the laboratory parameters (hematology and serum chemistry) were small and not appreciably different across formulations. No significant shifts from normal to abnormal laboratory values (hematology and serum chemistry) were observed for either group during the study. No clinically significant changes in the vital signs were noted at the end of study compared to baseline in the study. The changes in the physical examination results at the end of study compared to baseline were minimal. No significant physical findings were noted during the study. No significant shifts from normal to abnormal neurological results were observed for either group during the study.

Summary

The primary outcome of the clinical study, pain severity, was met as there was a significant difference in ranked scores between formulations in favor of the 20 mg/0.5 ml formulation of GA. Mean LISR presence and severity scores were low for both formulations, indicating that injection site reactions were relatively infrequent and when present, not severe in most cases. Similar to the VAS findings, the ranked scores for injection site reaction measures significantly favored the 20 mg/0.5 ml formulation of GA. Both formulations showed a good tolerability and safety profile. Since injection site reactions, including pain, are the most frequently reported adverse events in subjects receiving daily injections of GA for RRMS, the 20 mg/0.5 ml may offer clinical benefits for some patients. Having comparable efficacy, the 20 mg/0.5 ml GA formulation may be advantageous to patients with RRMS who require daily injections, as subjects in this study reported less pain and fewer injection site reactions following use of this formulation in comparison with the 20 mg/1.0 ml GA formulation.

REFERENCES

1. Noseworthy J H, Lucchinetti C, Rodriguez M, Weinshenker B G. Multiple sclerosis. N Engl J Med 2000; 343:938-52.
2. Guideline on clinical investigation of medicinal products for the treatment of multiple sclerosis EMEA, London 16 Sep. 2006.
3. Bjartmar C, Fox R J. Pathological mechanisms and disease progression of multiple sclerosis: therapeutic implications. Drugs of Today 2002; 38:17-29.
4. Fleming J O. Diagnosis and management of multiple sclerosis. 1st ed. New York: Professional communications, Inc., 2002.
5. Anderson D W, Ellenberg J H, Leventhal C M et al. Revised estimate of the prevalence of multiple sclerosis in the United States. Ann Neurol 1992; 31:333-36.
6. Compston A, Lassmann H, McDonald I. The story of multiple sclerosis. In: Compston A, Confavreux C, Lassman H, Mcdonald I, Miller D, Noseworthy J H, Smith K, Wekerle H, editors. McAlpine's Multiple Sclerosis. London: Churchill Livingstone; 2006. p. 3-68.
7. Arnon, R, Aharoni, R. Neurogenesis and neuroprotection in the CAN-Fundamental elements in the effect of glatiramer acetate in treatment of autoimmune neurological disorders. *Mol Nenrobiol* 2007; 36:245-53.
8. Ruggiere, M, Avolio, C, Livrea, P, et al. Glatiramer acetate in multiple sclerosis: A review. *CNS Drug Reviews* 2007; 13(2): 178-91.
9. Weber, M S, Hohfeld, R, Zamvil, S S. Mechanism of action of glatiramer acetate in treatment of multiple sclerosis. *Neurotherapeutics* 2007; 4(4):647-53.
10. Ziemssen, T, Schrempf, W. Glatiramer acetate: Mechanisms of action in multiple sclerosis. *International Rev of Neurobiol* 2007; 79:537-70.
11. Dhib-Jalbut S. Glatiramer acetate (Copaxone) therapy for multiple sclerosis. Pharmacol Ther 2003; 98:245-55.
12. Dhib-Jalbut S. Mechanisms of action of interferons and glatiramer acetate in multiple sclerosis. Neurology 2002; 58(Suppl 4):S3-S9.
13. Bornstein, M B, Miller, A, Slagle, S, et al. A pilot trial of Cop 1 in exacerbating remitting multiple sclerosis. *New Eng J Med* 1987; 317: 408-14.
14. Comi, G, Fillippi, M, Wolinsky, J S, et al. European/Canadian multicenter, double-blind, randomized, placebo-controlled study of the effects of glatiramer acetate on magnetic resonance imagine-measured disease activity and burden in patients with relapsing multiple sclerosis. *Ann Neurol* 2001; 49: 290-7.

15. Johnson, K P, Brooks, B R, Cohen, J A, et al. Extended use of glatiramer acetate (Copaxone) is well tolerated and maintains its clinical effect on multiple sclerosis relapse rate and degree of disability. *Neurology* 1998; 50:701-8.
16. Bornstein, M B, Miller, A, Slagle, S, et al. A placebo-controlled, double-blind, randomized, two-center, pilot trial of Cop-1 in chronic progressive multiple sclerosis. *Neurology* 1991; 41: 533-39.
17. Wolinsky, J S, Narayana, P A, O'Conner, P, at al. Glatiramer acetate in primary progressive multiple sclerosis: Results of a multinational, multicenter, double-blind, placebo-controlled trial. *Ann Neurol* 2007; 61:14-24.
18. Tselis, A, Khan, O, Lisak, R P, Glatiramer acetate in the treatment of multiple sclerosis. *Neuropsychiatric Dis Treat* 2007; 3(2):259-67.
19. Wolinsky, J S, The use of glatiramer acetate in the treatment of multiple sclerosis. *Adv Neurol* 2006; 273-92.
20. Comi G, Filippi M, Treatment with glatiramer acetate delays conversion to clinically definite multiple sclerosis (CDMS) in patients with clinically isolated syndromes (CIS). *Neurology* 2008; 71 (2): 153.
21. Stark et al., PCT International Publication No. WO/2009/070298, published Jun. 4, 2009.
22. Comi G, Cohen J A, Filippi M, Results from a phase III, one-year, randomized, double-blind, parallel-group, dose-comparison study with glatiramer acetate in relapsing-remitting multiple sclerosis. *Mult Scler* 2008; 14(suppl 1):S299.
23. Comi G, Filippi M. Presented at: 60th Annual Meeting of the American Academy of Neurology: April 12-19; Chicago, Ill. Abstract LBS.003.
24. Periodic Safety Update Report, Copaxone® (glatiramer acetate for injection): 1 Dec. 2007-30 Nov. 2008. Teva Pharmaceutical Industries Ltd., January 2009.
25. Shire S J, Shahrokh Z, Liu J, Challenges in the Development of High Protein Concentration Formulations. *J Pharm Sci*, 2004; 93(6): 1390-1402.
26. Kansara V, Mitra A, Wu Y, Subcutaneous Delivery. Drug Deliv Technol, June 2009; 9(6):38-42.
27. Product Monograph, Copaxone, Revised Apr. 14, 2009: 1-35.
28. Johnson D, Hafler D A, Fallis R J, Lees M B, Brady R O, Quarles R H, Weiner H L., "Cell-mediated immunity to myelin-associated glycoprotein, proteolipid protein, and myelin basic protein in multiple sclerosis.", *J. Neuroimmunol.* 1986 November; 13 (1):99-108.
29. Brex P A et al., "A longitudinal study of abnormalities on MRI and disability from multiple sclerosis", *N Engl J Med* 2002 Jan. 17, 346(3):158-64.
30. Frohman E M et al., "The utility of MRI in suspected MS: report of the Therapeutics and Technology Assessment Subcommittee of the American Academy of Neurology", *Neurology,* 2003, September 9, 61(5):602-11.
31. Marrie R A, "Environmental risk factors in multiple sclerosis aetiology", Lancet Neurol. 2004 December, 3(12): 709-18.
32. Ascherio A, Munger K L, "Environmental risk factors for multiple sclerosis. Part I: the role of infection", Ann Neurol, 2007 April, 61(4):288-99.
33. Ascherio A, Munger K L, "Environmental risk factors for multiple sclerosis. Part II: non-infectious factors", Ann Neurol, 2007 July, 61(6):504-13.
34. Niino M, "Recent advances in genetic analysis of multiple sclerosis: genetic associations and therapeutic implications", Expert Rev Neurother, 2007, September, 2(9):1175-88.
35. Reich D, "A whole-genome admixture scan finds a candidate locus for multiple sclerosis susceptibility", Nat Genet, 2005, October, 37(10):1113-8, Epub 2005, Sep. 25.
36. McFarland H F, "Multiple sclerosis: a complicated picture of autoimmunity", Nat Immunol, 2007, September (9): 913-9.
37. Lutterotti A, "Biological markers for multiple sclerosis", CurrMedChem, 2007, 14(18):1956-65.
38. Rinaldi L. and Gallo P., "Immunological markers in multiple sclerosis: tackling the missing elements", Neurol Sci, 2005, 26: 5215-5217.
39. Copaxone® (glatiramer acetate injection), prescribing information, www.copaxone.com/pdf/PrescribingInformation.pdf, February, 2009
40. Cohen et al., Randomized, double-blind, dose-comparison study of glatiramer acetate in relapsing-remitting MS, Neurology, 2007; 68:939-944.
41, U.S. Patent Application Publication No. 2007/0161566 A1 to Pinchasi.
42. Teva Provides Update on FORTE Trial, Teva News & PR, Press Release, Jul. 7, 2008.

What is claimed is:

1. An aqueous pharmaceutical solution which is 0.5 ml in volume and contains 20 mg glatiramer acetate and 20 mg mannitol in water for injection.

2. The aqueous pharmaceutical solution of claim 1, wherein the pH of the aqueous pharmaceutical solution is 5.5 to 7.0.

3. The aqueous pharmaceutical solution of claim 1, wherein the 0.5 ml aqueous pharmaceutical solution is in a pre-filled syringe.

4. A pre-filled syringe which contains 0.5 ml of an aqueous pharmaceutical solution of 20 mg glatiramer acetate and 20 mg mannitol.

5. The pre-filled syringe of claim 4, wherein the pH of the aqueous pharmaceutical solution is 5.5 to 7.0.

6. A pre-filled syringe which contains 0.5 ml of an aqueous pharmaceutical solution of 20 mg glatiramer acetate and 20 mg mannitol, wherein the pH of the aqueous pharmaceutical solution is 5.5 to 7.0, and wherein the 20 mg of glatiramer acetate does not form polypeptide aggregates in the 0.5 ml of aqueous pharmaceutical solution.

* * * * *